United States Patent
Kruzel et al.

(10) Patent No.: US 10,442,852 B2
(45) Date of Patent: Oct. 15, 2019

(54) METHODS AND COMPOSITIONS FOR TREATMENT OF SYMPTOMS ASSOCIATED WITH INTRACRANIAL HEMORRHAGE

(71) Applicant: BOARD OF REGENTS OF THE UNIVERSITY OF TEXAS SYSTEM, Austin, TX (US)

(72) Inventors: Marian L. Kruzel, Houston, TX (US); Jaroslaw Aronowski, Houston, TX (US)

(73) Assignee: BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/847,719

(22) Filed: Dec. 19, 2017

(65) Prior Publication Data

US 2018/0127486 A1 May 10, 2018

Related U.S. Application Data

(63) Continuation-in-part of application No. PCT/US2016/039362, filed on Jun. 24, 2016.

(60) Provisional application No. 62/184,049, filed on Jun. 24, 2015.

(51) Int. Cl.
| | |
|---|---|
| *C07K 16/00* | (2006.01) |
| *C07K 14/79* | (2006.01) |
| *A61P 9/00* | (2006.01) |
| *A61K 38/00* | (2006.01) |

(52) U.S. Cl.
CPC .......... *C07K 14/79* (2013.01); *A61P 9/00* (2018.01); *C07K 16/00* (2013.01); *A61K 38/00* (2013.01); *C07K 2317/21* (2013.01); *C07K 2317/41* (2013.01); *C07K 2317/53* (2013.01); *C07K 2319/30* (2013.01)

(58) Field of Classification Search
None
See application file for complete search history.

(56) References Cited

U.S. PATENT DOCUMENTS

| | | |
|---|---|---|
| 2004/0265973 A1 | 12/2004 | Sun et al. |
| 2011/0092677 A1 | 4/2011 | Sadeghi et al. |
| 2011/0182898 A1* | 7/2011 | Karrer .............. C07K 14/70521 424/134.1 |
| 2013/0108580 A1* | 5/2013 | Leder .................... C12N 15/62 424/85.1 |
| 2015/0093382 A1 | 4/2015 | Sato et al. |
| 2015/0247135 A1* | 9/2015 | Hill ...................... C07K 14/475 435/194 |

FOREIGN PATENT DOCUMENTS

| | | |
|---|---|---|
| WO | 2006/096515 A2 | 9/2006 |
| WO | 2015/005748 A1 | 1/2015 |

OTHER PUBLICATIONS

Wang et al., Novel GLP-1 Fusion Chimera as Potent Long Acting GLP-1 Receptor Agonist, Sep. 2010, PLoS ONE vol. 5, Issue 9, e12734, 9 pages. (Year: 2010).*
Chen et al., Fusion protein linkers: Property, design and functionality, 2013, Advanced Drug Delivery Reviews 65:1357-1369 (Year: 2013).*
International Patent Application No. PCT/US2016/039362 International Search Report and Written Opinion dated Sep. 27, 2016 (16 pages).
Shiga, Yuki et al., "Recombinant human lactoferrin-Fc fusion with an improved plasma half-life," European Journal of Pharmaceutical Sciences, Nov. 26, 2014 (online), vol. 67, pp. 136-143.
Conesa, Celia et al., "Recombinant human lactoferrin: A valuable protein for pharmaceutical products and function foods," Biotechnology Advances, 2010, vol. 28, pp. 831-838.
Extended European Search Report issued in European Application No. 16815424.3, dated Nov. 28, 2018.
Kruzel, Marian L., et al. "Novel Recombinant Human Lactoferrin: Differential Activation of Oxidative Stress Related Gene Expression." *Journal of Biotechnology* 168.4 (2013): 666-675.

* cited by examiner

*Primary Examiner* — John D Ulm
(74) *Attorney, Agent, or Firm* — Parker Highlander PLLC

(57) ABSTRACT

Methods and compositions are provided for the treatment of a patient with intracranial hemorrhage (ICH). Methods include the use of the products of recombinant constructs such as those that contain lactoferrin, as well as fusion protein constructs of lactoferrin and Fc domain for IgG.

11 Claims, 22 Drawing Sheets

Specification includes a Sequence Listing.

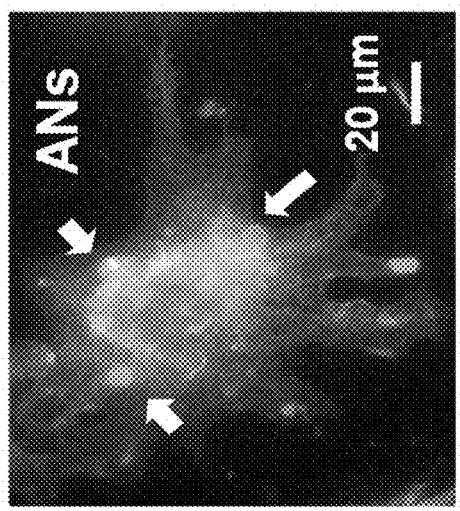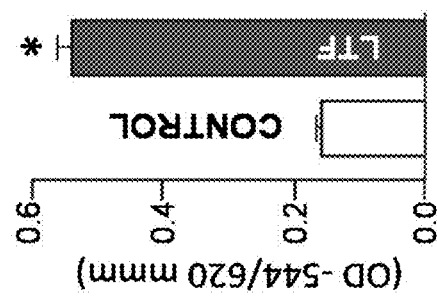
FIG. 7

Networks of genes with similar up/down regulation patterns.

| # | Molecules in Network | Score | Top Functions |
|---|---|---|---|
| 1 | Adaptor protein 1, ALT, Chr, CD80, CD80/CD86, Collagen type VI, Collagen type I, CD82, cyclooxygenase, Estrane, ERK1/2, Fc gamma receptor, Fcer1, Fcgr3, Ferritin, Gm-csf, HLA-DQ, HLA-DR, Ige, IgG1, IgG2b, IL6 (family), IL17 dimer, IL5R, IL7/IL6/TNF, IL17 dimer, ILA, MAX, IRF, lymphotoxin-alpha1-beta2, myosin light chain kinase, SCAVENGER receptor CLASS A, Spnb, TLR7, TLR9 | 4 | Cellular Development, Hematopoiesis, Cell-To-Cell Signaling and Interaction |
| 2 | 26s Proteasome, Actin, Alp, Alpha catenin, AMPK, caspase, Caspase 3/7, Cg, chemokine, CK2, Collagen type I, Creb, CYP, cytochrome C, Histone h3, Hsp70, Hsp90, Ifn, IFNG, IL6, IL12 (family), IL1B, Mhc, Mmp, NFkB (complex), Nos, P38 (complex), PRKAA, RNA polymerase II, Secretase gamma, Smad, Sod, STAT5a/b, Tnf (family), Tnl | 3 | Cellular Development, Embryonic Development, Organismal Development |
| 3 | Aconitase, Angiotensin II receptor type 1, C/ebp, Cebp, CXCL13, elastase, Growth hormone, Hdac, HDL, Histone h4, IFN alpha/beta, IFN BETA, Ifn gamma, IFN type 1, Ifnar, Igs, IgG2a, IL23, IL12 (complex), MHC Class I (complex), MHC CLASS I (family), N-cor, NFkB (family), MRB-RelA, Notch, Nr1h, P38 (family), Pro-inflammatory Cytokine, Rxr, SAA, sphingomyelinase, TH1Cytokine, Tn, TNF, Tnf receptor | 2 | Lipid Metabolism, Small Molecule Biochemistry, Vitamin and Mineral Metabolism |
| 4 | Akt, Ass1, BCR (complex), calpain, CD3, CD40LG, collagen, Cyclin A, Cyclin E, Fibrinogen, GOT, Hsp27, Hsp70, IgG, IgG3, IgM, Ikb, IL1, IKr, immunoglobulin, interferon alpha, MMK1/2, Ldh (complex), LDL, MAP2K1/2, Mek, MHC Class II (complex), NFAT (complex), Nfat (family), p70 S6k, Sapk, TCR, Tgf beta, TH2 Cytokine, TSH, VAV | 1 | Antigen Presentation, Cancer, Cell Death and Survival |
| 5 | ABI3BP, ANGPTL7, Collagen(s), ERK, estrogen receptor, ETV2, Focal adhesion kinase, ganglioside GD2, GSK3, HISTONE, IKK (complex), Insulin, Jnk, Lh, Mapk, miR-149-5p (miRNAs w/seed CUGGGCU), MUC5, NKURL, NKUR2, Oboe4, OPTC, p38 MAPK, PAK3, Pka, PLA2, PLC, Prosmulin, Ptprs, Rac, Ras, Ras homolog, SRE (family), STAT, THEMIS2, Vegf | 0 | Carbohydrate Metabolism, Small Molecule Biochemistry, Cancer |

FIG. 14

SEQUENCE LISTING

```
<160> NUMBER OF SEQ ID NOS: 8

<210> SEQ ID NO 1
<211> LENGTH: 2837
<212> TYPE: DNA
<213> ORGANISM: Artificial sequence
<220> FEATURE:
<223> OTHER INFORMATION: Synthetic oligonucleotide

<400> SEQUENCE: 1
aattgccgcc accatgaagc tggtgtttct cgtgctgctg tttctgggag ccctgggact      60
ctgtctcgct ggtagacgcc gacggagtgt gcagtggtgt gctgtgtccc agcccgaggc     120
aacaaagtgc ttccagtggc agagaaatat gcggaaagtg cgcggccccc ctgtcagttg     180
cattaagcgc gactcaccta tccagtgtat tcaggccatc gctgaaaacc gagcagacgc     240
```

```
cgtgactctg gatggcggct tcatctacga ggcaggtctc gccccttata agctgagacc    300
agtggccgct gaagtctacg gcaccgagcg acagccaagg acacactact atgctgtggc    360
agtggtcaag aaaggggta gtttccagct gaatgagctc cagggcctga agtcatgcca    420
taccgggctg aggagaacag ccggttggaa tgtgcccatt ggcactctcc ggccttttct    480
gaactggacc ggaccaccag aacctatcga ggcagcagtg gcacgcttct tttccgcttc    540
ttgtgtccct ggggccgaca aaggccagtt cccaaatctc tgccggctgt gtgcagggac    600
tggtgaaaac aagtgcgcct ttagctccca ggagccatac ttcagttatt caggcgcctt    660
taaatgtctg agagacggcg ctggagatgt ggcattcatt cgggaatcaa ccgtctttga    720
ggacctgagc gatgaagccg agcgcgacga atacgagctg ctctgcccag ataacacacg    780
aaagcccgtg acaagttca agattgtca cctggctcgg gtgccttccc atgctgtggt    840
cgcacgctct gtcaatggga agaagatgc tatctggaac ctgctcagac aggcacagga    900
gaagtttggc aaggacaaaa gccccaaatt ccagctgttt ggcagccctt ccggacagaa    960
ggacctgctc ttcaaagatt ccgccattgg attttctaga gtgcctccac ggatcgatag   1020
cgggctgtac ctcgggtccg gttatttcac agctattcag aatctgagga agagcgagga   1080
agaggtggct gcacgacgag caagagtggt ctggtgcgct gtcggggaac aggagctccg   1140
gaaatgtaac cagtggtcag ggctgagcga gggttccgtg acttgctcta gtgccagcac   1200
cacagaagac tgtatcgctc tggtgctcaa gggagaggca gacgctatga gcctggatgg   1260
cggatacgtg tataccgcag gcaaatgcgg actcgtgcct gtcctggccg aaaattacaa   1320
gtctcagcag tcaagcgacc ccgatcctaa ctgtgtggat cggccagtcg agggatatct   1380
cgcagtggcc gtggtccgaa ggtctgacac aagtctgact tggaactctg tgaaggggaa   1440
gaaaagttgc cacactgcag tcgaccgcac cgccggatgg aatattccca tggggctgct   1500
cttcaaccag accggatcct gcaagttcga cgagtacttt tctcagagtt gtgctccagg   1560
gtcagatccc aggagcaatc tctgcgcact gtgtatcggc gacgaacagg gagagaacaa   1620
gtgcgtgcct aattctaacg aacgatacta tgggtataca ggtgccttca ggtgtctggc   1680
cgagaatgct ggtgacgtgg cttttgtcaa ggatgtgaca gtcctgcaga acactgatgg   1740
aaacaataac gaggcttggg caaaggacct gaaactcgca gatttcgccc tgctctgcct   1800
ggacggaaag aggaaaccag tgaccgaagc cagatcttgt cacctggcca tggctcccaa   1860
ccatgctgtg gtcagtcgca tggataaggt gggagcgactg aaacaggtcc tgctccacca   1920
gcaggccaag ttcggcagga atggaagcga ctgccctgat aagttctgtc tgtttcagtc   1980
cgaaacaaaa aacctgctct ttaatgacaa cactgagtgt ctcgccagac tgcatggcaa   2040
gactacctac gagaaatatc tgggtcccca gtacgtggct ggcatcacaa acctgaagaa   2100
gtgctctacc tcacctctcc tggaagcctg cgagttcctg cgaaaggat ccgagcgcaa   2160
atgttgcgtg gagtgccctc cctgtccgc tcctcccgtg gccggaccct cagtcttcct   2220
cttcccaccc aaacccaagg acaccctcat gatctcccgg acccctgagg tcacatgcgt   2280
ggtggtggac gtgagccacg aagaccctga ggtccagttc aactggtacg tggacggcgt   2340
ggaggtgcat aatgccaaga caaagccgcg ggaggagcag ttcaacagca cgttccgtgt   2400
ggtcagcgtc ctcaccgtcg tgcaccagga ctggctgaat ggcaaggagt acaagtgcaa   2460
ggtctccaac aaaggcctcc cagctcccat cgagaaaacc atctccaaaa ccaaagggca   2520
gccctcgagaa ccacaggtgt acaccctgcc tccctctcgg gaggagatga ccaagaacca   2580
```

```
ggtcagcctg acctgcctgg tcaaaggctt ctatcccagc gacatcgccg tggagtggga    2640
gagcaatggg cagccggaga acaactacaa gaccacgcct cccatgctgg actccgacgg    2700
ctccttcttc tctctatagca agctcaccgt ggacaagagc aggtggcagc aggggaacgt    2760
cttctcatgc tccgtgatgc atgaggctct gcacaaccac tacacgcaga gagcctctc    2820 cctgtctccg ggtaaat                                                   2837
```

<210> SEQ ID NO 2
<211> LENGTH: 941
<212> TYPE: PRT
<213> ORGANISM: Artificial sequence
<220> FEATURE:
<223> OTHER INFORMATION: Synthetic polypeptide

<400> SEQUENCE: 2

```
Met Lys Leu Val Phe Leu Val Leu Leu Phe Leu Gly Ala Leu Gly Leu
1               5                   10                  15

Cys Leu Ala Gly Arg Arg Arg Ser Val Gln Trp Cys Ala Val Ser
            20                  25                  30

Gln Pro Glu Ala Thr Lys Cys Phe Gln Trp Gln Arg Asn Met Arg Lys
        35                  40                  45

Val Arg Gly Pro Pro Val Ser Cys Ile Lys Arg Asp Ser Pro Ile Gln
    50                  55                  60

Cys Ile Gln Ala Ile Ala Glu Asn Arg Ala Asp Ala Val Thr Leu Asp
65                  70                  75                  80

Gly Gly Phe Ile Tyr Glu Ala Gly Leu Ala Pro Tyr Lys Leu Arg Pro
                85                  90                  95

Val Ala Ala Glu Val Tyr Gly Thr Glu Arg Gln Pro Arg Thr His Tyr
            100                 105                 110

Tyr Ala Val Ala Val Val Lys Lys Gly Gly Ser Phe Gln Leu Asn Glu
        115                 120                 125

Leu Gln Gly Leu Lys Ser Cys His Thr Gly Leu Arg Arg Thr Ala Gly
    130                 135                 140

Trp Asn Val Pro Ile Gly Thr Leu Arg Pro Phe Leu Asn Trp Thr Gly
145                 150                 155                 160

Pro Pro Glu Pro Ile Glu Ala Ala Val Ala Arg Phe Phe Ser Ala Ser
                165                 170                 175

Cys Val Pro Gly Ala Asp Lys Gly Gln Phe Pro Asn Leu Cys Arg Leu
            180                 185                 190

Cys Ala Gly Thr Gly Glu Asn Lys Cys Ala Phe Ser Ser Gln Glu Pro
        195                 200                 205

Tyr Phe Ser Tyr Ser Gly Ala Phe Lys Cys Leu Arg Asp Gly Ala Gly
    210                 215                 220

Asp Val Ala Phe Ile Arg Glu Ser Thr Val Phe Glu Asp Leu Ser Asp
225                 230                 235                 240

Glu Ala Glu Arg Asp Glu Tyr Glu Leu Leu Cys Pro Asp Asn Thr Arg
                245                 250                 255

Lys Pro Val Asp Lys Phe Lys Asp Cys His Leu Ala Arg Val Pro Ser
            260                 265                 270

His Ala Val Val Ala Arg Ser Val Asn Gly Lys Glu Asp Ala Ile Trp
        275                 280                 285

Asn Leu Leu Arg Gln Ala Gln Glu Lys Phe Gly Lys Asp Lys Ser Pro
    290                 295                 300

Lys Phe Gln Leu Phe Gly Ser Pro Ser Gly Gln Lys Asp Leu Leu Phe
305                 310                 315                 320
```

```
Lys Asp Ser Ala Ile Gly Phe Ser Arg Val Pro Arg Ile Asp Ser
            325                 330                 335

Gly Leu Tyr Leu Gly Ser Gly Tyr Phe Thr Ala Ile Gln Asn Leu Arg
            340                 345                 350

Lys Ser Glu Glu Val Ala Ala Arg Ala Arg Val Val Trp Cys
        355                 360                 365

Ala Val Gly Glu Gln Glu Leu Arg Lys Cys Asn Gln Trp Ser Gly Leu
        370                 375                 380

Ser Glu Gly Ser Val Thr Cys Ser Ser Ala Ser Thr Thr Glu Asp Cys
385                 390                 395                 400

Ile Ala Leu Val Leu Lys Gly Glu Ala Asp Ala Met Ser Leu Asp Gly
            405                 410                 415

Gly Tyr Val Tyr Thr Ala Gly Lys Cys Gly Leu Val Pro Val Leu Ala
            420                 425                 430

Glu Asn Tyr Lys Ser Gln Gln Ser Ser Asp Pro Asp Pro Asn Cys Val
            435                 440                 445

Asp Arg Pro Val Glu Gly Tyr Leu Ala Val Ala Val Val Arg Arg Ser
        450                 455                 460

Asp Thr Ser Leu Thr Trp Asn Ser Val Lys Gly Lys Lys Ser Cys His
465                 470                 475                 480

Thr Ala Val Asp Arg Thr Ala Gly Trp Asn Ile Pro Met Gly Leu Leu
                485                 490                 495

Phe Asn Gln Thr Gly Ser Cys Lys Phe Asp Glu Tyr Phe Ser Gln Ser
            500                 505                 510

Cys Ala Pro Gly Ser Asp Pro Arg Ser Asn Leu Cys Ala Leu Cys Ile
        515                 520                 525

Gly Asp Glu Gln Gly Glu Asn Lys Cys Val Pro Asn Ser Asn Glu Arg
        530                 535                 540

Tyr Tyr Gly Tyr Thr Gly Ala Phe Arg Cys Leu Ala Glu Asn Ala Gly
545                 550                 555                 560

Asp Val Ala Phe Val Lys Asp Val Thr Val Leu Gln Asn Thr Asp Gly
                565                 570                 575

Asn Asn Asn Glu Ala Trp Ala Lys Asp Leu Lys Leu Ala Asp Phe Ala
            580                 585                 590

Leu Leu Cys Leu Asp Gly Lys Arg Lys Pro Val Thr Glu Ala Arg Ser
        595                 600                 605

Cys His Leu Ala Met Ala Pro Asn His Ala Val Val Ser Arg Met Asp
        610                 615                 620

Lys Val Glu Arg Leu Lys Gln Val Leu Leu His Gln Gln Ala Lys Phe
625                 630                 635                 640

Gly Arg Asn Gly Ser Asp Cys Pro Asp Lys Phe Cys Leu Phe Gln Ser
                645                 650                 655

Glu Thr Lys Asn Leu Leu Phe Asn Asp Asn Thr Glu Cys Leu Ala Arg
            660                 665                 670

Leu His Gly Lys Thr Thr Tyr Glu Lys Tyr Leu Gly Pro Gln Tyr Val
        675                 680                 685

Ala Gly Ile Thr Asn Leu Lys Lys Cys Ser Thr Ser Pro Leu Leu Glu
        690                 695                 700

Ala Cys Glu Phe Leu Arg Lys Gly Ser Glu Arg Lys Cys Cys Val Glu
705                 710                 715                 720

Cys Pro Pro Cys Pro Ala Pro Pro Val Ala Gly Pro Ser Val Phe Leu
                725                 730                 735
```

```
Phe Pro Pro Lys Pro Lys Asp Thr Leu Met Ile Ser Arg Thr Pro Glu
                740                 745                 750

Val Thr Cys Val Val Val Asp Val Ser His Glu Asp Pro Glu Val Gln
            755                 760                 765

Phe Asn Trp Tyr Val Asp Gly Val Glu Val His Asn Ala Lys Thr Lys
        770                 775                 780

Pro Arg Glu Glu Gln Phe Asn Ser Thr Phe Arg Val Val Ser Val Leu
785                 790                 795                 800

Thr Val Val His Gln Asp Trp Leu Asn Gly Lys Glu Tyr Lys Cys Lys
                805                 810                 815

Val Ser Asn Lys Gly Leu Pro Ala Pro Ile Glu Lys Thr Ile Ser Lys
            820                 825                 830

Thr Lys Gly Gln Pro Arg Glu Pro Gln Val Tyr Thr Leu Pro Pro Ser
        835                 840                 845

Arg Glu Glu Met Thr Lys Asn Gln Val Ser Leu Thr Cys Leu Val Lys
850                 855                 860

Gly Phe Tyr Pro Ser Asp Ile Ala Val Glu Trp Glu Ser Asn Gly Gln
865                 870                 875                 880

Pro Glu Asn Asn Tyr Lys Thr Thr Pro Pro Met Leu Asp Ser Asp Gly
                885                 890                 895

Ser Phe Phe Leu Tyr Ser Lys Leu Thr Val Asp Lys Ser Arg Trp Gln
            900                 905                 910

Gln Gly Asn Val Phe Ser Cys Ser Val Met His Glu Ala Leu His Asn
        915                 920                 925

His Tyr Thr Gln Lys Ser Leu Ser Leu Ser Pro Gly Lys
930                 935                 940

<210> SEQ ID NO 3
<211> LENGTH: 15
<212> TYPE: PRT
<213> ORGANISM: Artificial sequence
<220> FEATURE:
<223> OTHER INFORMATION: Synthetic core hinge sequence derived from
      Human IgG1

<400> SEQUENCE: 3

Glu Pro Lys Ser Cys Asp Lys Thr His Thr Cys Pro Pro Cys Pro
1               5                   10                  15

<210> SEQ ID NO 4
<211> LENGTH: 12
<212> TYPE: PRT
<213> ORGANISM: Artificial sequence
<220> FEATURE:
<223> OTHER INFORMATION: Synthetic core hinge sequence derived from
      Human IgG2

<400> SEQUENCE: 4

Glu Arg Lys Cys Cys Val Glu Cys Pro Pro Cys Pro
1               5                   10

<210> SEQ ID NO 5
<211> LENGTH: 61
<212> TYPE: PRT
<213> ORGANISM: Artificial sequence
<220> FEATURE:
<223> OTHER INFORMATION: Synthetic core hinge sequence derived from
      Human IgG3

<400> SEQUENCE: 5

Glu Leu Lys Thr Pro Leu Asp Thr Thr His Thr Cys Pro Arg Cys Pro
```

```
1               5                   10                  15
Glu Pro Lys Ser Cys Asp Thr Pro Pro Pro Cys Pro Arg Cys Pro Glu
                20                  25                  30

Pro Lys Ser Cys Asp Thr Pro Pro Pro Cys Pro Arg Cys Pro Glu Pro
            35                  40                  45

Lys Ser Cys Asp Thr Pro Pro Pro Cys Pro Arg Cys Pro
    50                  55                  60

<210> SEQ ID NO 6
<211> LENGTH: 12
<212> TYPE: PRT
<213> ORGANISM: Artificial sequence
<220> FEATURE:
<223> OTHER INFORMATION: Synthetic core hinge sequence derived from
      Human IgG4

<400> SEQUENCE: 6

Glu Ser Lys Tyr Gly Pro Pro Cys Pro Ser Cys Pro
1               5                   10

<210> SEQ ID NO 7
<211> LENGTH: 127
<212> TYPE: DNA
<213> ORGANISM: Artificial sequence
<220> FEATURE:
<223> OTHER INFORMATION: Synthetic oligonucleotide

<400> SEQUENCE: 7
gtaaaacgac ggccagtgaa ttcgagctcg gtacctcgcg aatgcatcta gatatcggat        60
cccgggcccg tcgactgcag aggcctgcat gcaagcttgg cgtaatcatg gtcatagctg       120
tttcctg                                                                 127

<210> SEQ ID NO 8
<211> LENGTH: 127
<212> TYPE: DNA
<213> ORGANISM: Artificial sequence
<220> FEATURE:
<223> OTHER INFORMATION: Synthetic oligonucleotide

<400> SEQUENCE: 8
cattttgctg ccggtcactt aagctcgagc catggagcgc ttacgtagat ctatagccta        60
gggcccgggc agctgacgtc tccggacgta cgttcgaacc gcattagtac cagtatcgac       120
aaaggac                                                                 127
```

METHODS AND COMPOSITIONS FOR TREATMENT OF SYMPTOMS ASSOCIATED WITH INTRACRANIAL HEMORRHAGE

CROSS-REFERENCE TO RELATED APPLICATIONS

The present application is a continuation-in-part of PCT/US2016/039362, filed Jun. 24, 2016, which claims priority to U.S. Provisional Patent Application No. 62/184,049 filed Jun. 24, 2015, titled "Methods And Compositions For Treatment Of Symptoms Associated With Intracranial Hemorrhage," each of which is hereby incorporated herein by reference in its entirety.

The sequence listing that is contained in the file named "UTSHP0345US_update_ST25.txt", which is 15 KB (as measured in Microsoft Windows®) and was created on Nov. 20, 2018, is filed herewith by electronic submission and is incorporated by reference herein.

FIELD OF THE DISCLOSURE

The present invention generally relates to methods and compositions useful as treatments directed at symptoms associated with intracranial hemorrhage (ICH) and other related disorders.

BACKGROUND OF THE TECHNOLOGY

Intracranial hemorrhage (ICH) is a major public health problem with the highest mortality rate of all stroke subtypes and long-term disability, and has no available FDA-approved therapies. Although the number of hospital admissions for intracranial hemorrhage has increased worldwide, mortality has not fallen. ICH causes instantaneous mass effect, disruption of surrounding brain, and often an early neurological death, and in case of subarachnoid hemorrhage delayed cerebral ischemia (DCI) and cerebral vasospasm. Intracranial hemorrhage (ICH) occurs when blood leaks or bursts from broken/diseased blood vessels inside or on the surface of the brain leading to brain damage and neurological damage. Following ICH, the deposited blood is damaging initially via compression of the brain tissue (mass effect) and then via noxious chemical effect of hematoma components on brain (including vascular) tissue. Blood deposition leads to toxicity of hemolytic products (e.g., iron), oxidative stress, pro-inflammatory responses, immune cell recruitment, proteolytic enzymes-mediated extracellular matrix modification, blood brain barrier disruption, and deadly cerebral edema. Due to multifactorial nature of the disease, specific therapies for ICH treatment have been elusive. Since there are no available therapies for ICH there is a longstanding and unmet need for an effective treatment.

Lactoferrin (LTF) also known as lactotransferrin, is a well-known endogenous glycoprotein that is multifunctional with anti-microbial and immunoregulatory functions capable of curbing the inflammatory response and promoting repair, in part through its effective sequestration of free iron as LTF falls within the transferrin family of iron binding glycoproteins. Lactoferrin is a well-conserved, monomeric 80-kDa single polypeptide chain glycoprotein of about 692 amino acid residues that is widely represented in various secretory fluids, such as milk, saliva, tears, bronchial, nasal secretions, intestinal secretions and also in the secondary granules of neutrophils. Lactoferrin is also present in secondary granules of granulocytes (polymorphonuclear leukocytes; PMNs) and is secreted by some acinar cells. Lactoferrin may be purified from milk or produced as a recombinant protein. Lactoferrin is a critical component in mediation of immune response, especially for coordinated interactions between innate and adaptive components and associated responses. Engagement of innate components leads to triggering of signal pathways to promote inflammation, ensuring that invading pathogens remain in check while the specific immune response is either generated or upregulated. Lactoferrin is a key molecule involved in these processes.

Lactoferrin is a well-conserved, monomeric 80-kDa single polypeptide chain glycoprotein organized in two highly homologous lobes, designated the N- and C-lobe, each capable of binding single ferric ion ($Fe^{3+}$). In this regard, lactoferrin is considered an antioxidant because its iron binding ability inhibits the iron-catalyzed formation of $H_2O_2$ and .OH. Ultimately, lactoferrin bound $Fe^{3+}$ is safely transported to the macrophage or other cells for intracellular utility or storage. LTF has also been implicated in immunoregulatory functions, with modulatory component in allergic responses and protection against insult-induced mitochondrial dysfunction.

Lactoferrin is also a well-known endogenous glycoprotein with anti-microbial and immunoregulatory functions, capable of curbing the inflammatory response and promoting repair through its effective sequestration of free iron. However, LTF has limited therapeutic potential because of its short half-life in the blood and its difficulty penetrating the blood-brain barrier.

LTF is therefore rapidly cleared from the circulation (half-life of a few minutes). Therefore, despite the various activities ascribed to lactoferrin, there remains a need for the development of an efficient lactoferrin construct that provides a robust therapeutic for the treatment of a mammal.

Recently lactoferrin fusion proteins have thus been disclosed in the prior art such as described in PCT/JP2013/062685, and US patent publication US20150093382, however, there is a need to further optimize endogenous LTF, and such fusion proteins to improve cognitive processes and neurological functions, as well as change cellular responses in the area of damage, such as the anti-inflammatory responses of microglia, reduced infiltration of neutrophils, and lowered extent of neuronal death.

SUMMARY OF THE INVENTION

Disclosed herein are compositions and methods useful for the prevention and treatment of symptoms associated with intracranial hemorrhage (ICH) and other related disorders. These compositions comprise various forms of lactoferrin as well as lactoferin fusion proteins, such as but not limited to human Lactoferrin (hLTF) with the Fc fragment of IgG which produces a novel fusion protein (PRC14). Thus, in order to optimize the therapeutic capacity of Lactoferrin and enhance its stability and bioavailability, the generation of the recombinant fusion protein PRC14 in some embodiments extends LTF bioavailability, and in some further embodiments increases therapeutic effectiveness.

In some embodiments disclosed herein are recombinant polypeptides comprising a lactoferrin coding sequence and an immunoglobulin IgG Fc domain coding sequence fused to the lactoferrin coding sequence. Some embodiments of the polypeptide further comprise an IgG hinge coding sequence, wherein the hinge coding sequence is located between the lactoferrin coding sequence and the Fc domain coding sequence, in a further embodiment the IgG Fc domain coding sequence is an immunoglobulin G2 (IgG2)

coding sequence, and in a still further embodiment the IgG hinge coding sequence is a an immunoglobulin G2 (IgG2) coding sequence. In some embodiments the coding sequences are human. In another embodiment of the polypeptide, the amino acid sequence comprises SEQ ID NO: 2, in a further embodiment the polypeptide is glycosylated to form a glycosylated polypeptide, and in a still further embodiment the glycosylated polypeptide is N-linked type. In some embodiments the polypeptide further comprises a linker sequence, wherein the linker comprises of two amino acids, and in another embodiment the linker comprises a GS sequence.

In some embodiments herein disclose is an isolated recombinant polynucleotide molecule comprising a nucleic acid sequence encoding a polypeptide comprising a lactoferrin coding sequence and an immunoglobulin IgG Fc domain coding sequence fused to the lactoferrin coding sequence. In another embodiment the polynucleotide further comprises an IgG hinge coding sequence, and in a further embodiment the IgG hinge coding sequence is an immunoglobulin G2 (IgG2) coding sequence. In some embodiments the coding sequences are human, and in other embodiments the nucleic acid sequence comprises SEQ ID NO: 1. In some embodiments core sequences for human IgG subtypes comprise IgG1 (SEQ ID NO:3); IgG2 (SEQ ID NO:4); IgG3 (SEQ ID NO:5); IgG4 (SEQ ID NO:6).

In other embodiments herein disclose an expression vector comprises a heterologous promoter sequence linked to a nucleic acid sequence encoding the polypeptide of claim 2. In some embodiments of the expression vector the nucleic acid sequence comprises SEQ ID NO: 1. In further embodiments the vector is expressed in a mammalian cell; a CHO cell; a yeast cell; or an insect cell. In some embodiments disclosed herein is a host cell, comprising a polynucleotide molecule encoding a polypeptide of claim 2, in further embodiments the polynucleotide molecule encodes the polypeptide of SEQ ID NO: 2. In another embodiment the host cell is a mammalian cell; a CHO cell; a yeast cell or an insect cell. In an embodiment herein disclosed is a composition comprising a polypeptide comprising a lactoferrin coding sequence and an immunoglobulin IgG Fc domain coding sequence fused to the lactoferrin coding sequence and a pharmaceutically acceptable carrier. In another embodiment of the composition the polypeptide comprises SEQ ID NO: 2, and in further embodiments of the composition the carrier is aqueous, saline or a powder. In a still further embodiment the composition is frozen or lyophilized.

A further embodiment discloses a method of treating or preventing intracranial hemorrhage or a related disorder in a subject, comprising administering to the subject an effective amount of a composition comprising a polypeptide wherein the polypeptide comprises a lactoferrin coding sequence and an immunoglobulin IgG Fc domain coding sequence fused to the lactoferrin coding sequence. In one embodiment of the method, the polypeptide is administered intrathecally, bucally, orally, topically, intradermally, subcutaneously, intranasally, intramuscularly, intravenously, intra-arterially, or directly into a tissue site. In a further embodiment, the related disorder is a cognitive or neurological deficit, inflammation, infection, edema or brain atrophy due to intracranial hemorrhage. In some embodiments optimizing endogenous LTF comprises an improvement in cognitive processes and neurological functions, as well as change cellular responses in the area of damage, such as the anti-inflammatory responses of microglia, reduced infiltration of neutrophils, and lowered extent of neuronal death. In some embodiments cognitive processes are brain operations that allow the performance of complex functions such as but not limited to memory, language and control over emotions among others.

BRIEF DESCRIPTION OF THE DRAWINGS

FIG. 7 depicts an immunohistochemical stain of rat neuronal cells. Top Panel: Phalloidin-FITC-labeled rat microglia (MMΦ; green) after efferocytosing the PKH26-labeled apoptotic neutrophils (ANs; red). Arrows indicate the engulfed ANs. Nuclei are stained with DAPI (blue). Bottom Panel: Efferocytosis Index of ANs at 4 h after exposure to PKH26-labeled ANs (mean±SEM, n=3). LTF (rhLTF) enhanced the efferocytosis of ANs. *p≤0.05.

FIG. 14 depicts the Network organization of genes with similar up/down regulation patterns.

DETAILED DESCRIPTION

Figure 1:
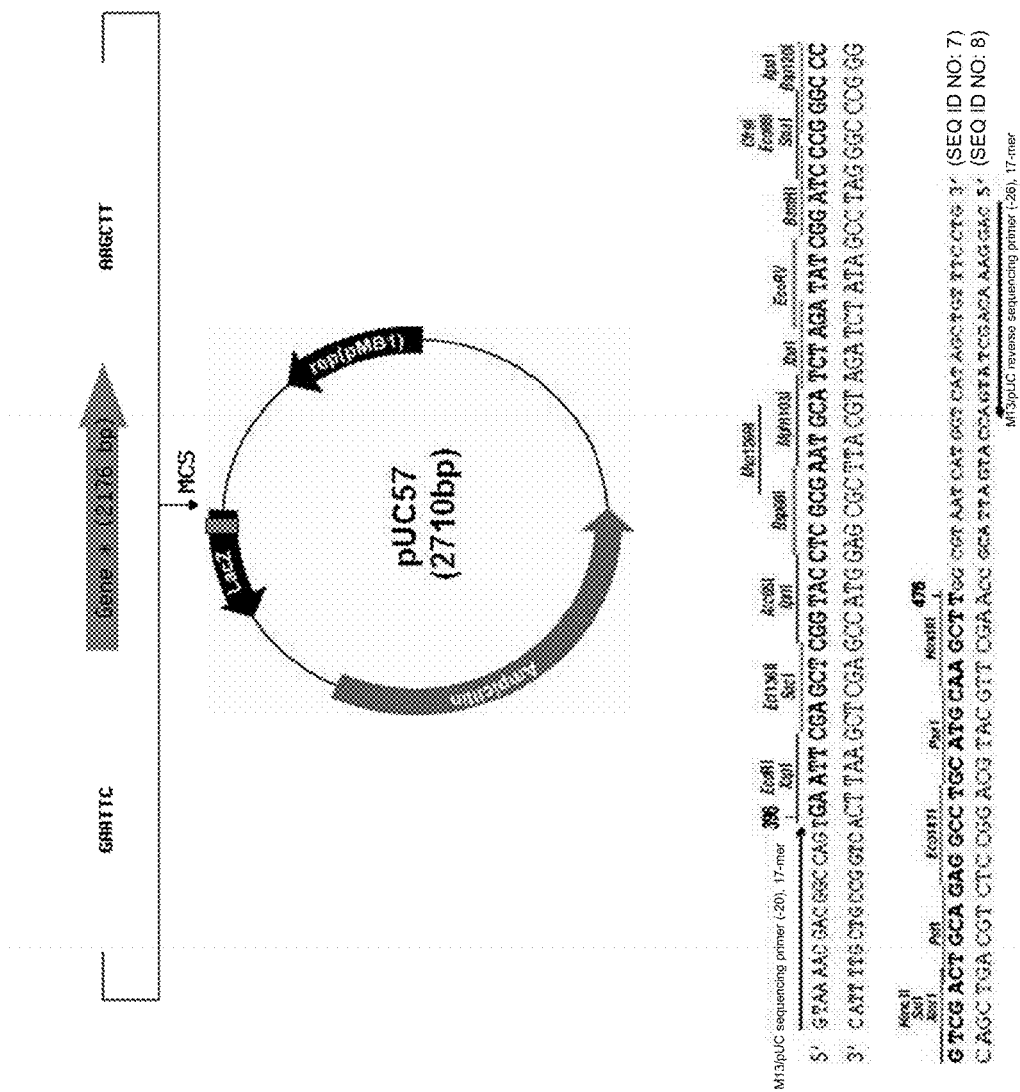
FIG. 1 depicts a vector pUC57 sequence and restriction enzyme map. The human lactoferrin human IgG2 Fc fusion gene was generated through overlap PCR and further subcloned into pUC57 using EcoRI and HindIII to generate pKN009-LF-hFc.

Embodiments of the disclosure are herein provided for treating or preventing intracranial hemorrhage (ICH) or a related disorder in a subject, wherein the method comprises administering to the subject an effective amount of a composition comprising a lactoferrin.

In various embodiments, lactoferrin is a recombinant polypeptide. In such embodiments, the lactoferrin is optimized as a fusion protein that comprises recombinant polypeptide comprising a lactoferrin coding sequence and a coding sequence from an Fc receptor for IgG.

In other embodiments, the disclosed methods may be used to treat a disorder that results in symptoms of brain edema or neurological deficit. In some embodiments, lactoferrin comprises a fusion polypeptide comprising a lactoferrin coding sequence and a coding sequence from a Fc domain of IgG2. For example, lactoferrin may comprises a fusion polypeptide comprising a human lactoferrin coding sequence; and the coding sequence from the human Fc domain of IgG2; or lactoferrin may comprise a polypeptide that comprises the amino acid sequence of SEQ ID NO: 2 of the lactoferrin fusion protein PRC14 (as detailed in the examples below). In various embodiments, the lactoferrin may be human lactoferrin or a fully humanized recombinant lactoferrin having N-type glycan linked to the polypeptide chain. In other embodiments recombinant lactoferrin may be expressed in bacterial, insect or mammalian cell based expression systems. In still further embodiments, expression of recombinant lactoferrin includes, but is not limited to, expression in bacterial, insect or mammalian cells such as, and further not limited to expression in Chinese hamster ovary or human cells.

In a further embodiment, an isolated polynucleotide molecule is provided that comprises a nucleic acid sequence encoding a lactoferrin polypeptide of the present embodiments. In some embodiments, recombinant polypeptide comprising a lactoferrin coding sequence and a coding sequence from a Fc domain of IgG2. In other embodiments the polypeptide is a fusion protein comprising a human lactoferrin coding sequence and the coding sequence from the human Fc domain of IgG2. In additional embodiments, the polypeptide comprises the nucleic acid sequence that encodes SEQ ID NO: 2, or the polypeptide comprises the nucleic acid sequence of SEQ ID NO: 1.

In some embodiments, the nucleic acid sequence encoding the polypeptide may be operably linked to a promoter. In certain embodiments, the promoter may be a promoter functional in mammalian, bacterial or insect cells. In some embodiments, the polynucleotide molecule may be part of an expression vector, such as, a plasmid, an episomal expression vector or a viral expression vector. In other embodiments the polynucleotide molecule comprising a nucleic acid sequence encoding a lactoferrin polypeptide described, such a nucleic acid sequence encoding the polypeptide is operably linked to a promoter. In some embodiments the promoter is a promoter that is functional in mammalian cells, and the polynucleotide is part of expression vector, such as a plasmid or viral expression vector.

In yet another embodiment, a host cell is provided that comprises a polynucleotide molecule encoding a lactoferrin polypeptide of the present embodiments. In some embodiments, the host cell may be a bacterial cell, an insect cell, or a mammalian cell. In some specific embodiments, the host cell is a human cell, such as a pluripotent cell.

In a further embodiment, a composition is provided that comprises polypeptides of the present embodiments in a pharmaceutically acceptable carrier. In various embodiments, the composition may be frozen or lyophilized. In various embodiments the carrier may be aqueous (such as but not limited to saline) or for example, a powder. In various embodiments such compositions are administered orally, topically, intradermally, subcutaneously, intramuscularly, intravenously, intra-arterially, intranasally, or directly into a tissue site.

In another embodiment, a method of treating or preventing intracranial hemorrhage or a related disorder in a subject comprising administering an effective amount of a composition comprising a polypeptide, a polynucleotide or a cell in accordance with the described embodiments. Such compositions comprising lactoferrin are administered orally, bucally, topically, intradermally, subcutaneously, intramuscularly, intravenously, intra-arterially, intranasally, intrathecally, or directly into a tissue site to a subject, such as but not limited to a companion animal or a human.

In still other embodiments, are compositions that comprise isolated recombinant human lactoferrin in aqueous solution or powder, wherein the lactoferrin has an ability to limit the neurological deficit, edema, brain atrophy and improve brain cleanup (to remove dead brain tissue and hematoma components) after ICH in humans. In another embodiment, the lactoferrin is human lactoferrin. In other embodiments the lactoferrin is recombinant human lactoferrin. In some embodiments, the lactoferrin is fully humanized recombinant human lactoferrin having N-type glycan linked to the protein chain. In additional embodiments, the recombinant human lactoferrin is expressed in a mammalian expression system. In some embodiments the mammalian expression system uses human epithelial kidney cell line. In other embodiments, the mammalian expression system uses Chinese hamster ovary cell line.

In some embodiments, a composition is disclosed herein that comprises an isolated fusion of human LTF with Fc domain for IgG (LTF-hIgG-Fc) in aqueous solution or powder, wherein the recombinant LTF-hIgG-Fc fusion protein has an ability to limit the neurological deficit, edema and brain atrophy caused by ICH in humans. In some embodiments, the recombinant LTF-hIgG-Fc fusion protein is a fusion of human LTF and human neonatal Fc receptor for IgG. In some embodiments, the recombinant LTF-hIgG-Fc fusion protein is expressed in mammalian expression system. In some embodiments the mammalian expression system uses human epithelial kidney cell line. In other embodiments, the mammalian expression system uses Chinese hamster ovary cell line.

Embodiments herein also disclose methods for using LTF to manage a neurological deficit, edema, brain cleanup, and brain atrophy due to ICH in a human in need of such a therapy. In other embodiments are methods for using recombinant LTF-Fc fusion proteins to manage a neurological deficit, edema and brain atrophy due to ICH in a human in need of such a therapy. In some embodiments methods of treating a patient with ICH with recombinant LTF to manage a neurological deficit, edema, brain cleanup, or brain atrophy are disclosed. In other embodiments are methods of treating a patient with ICH using a recombinant LTF-hIgG-Fc fusion protein to manage a related neurological deficit, edema, brain cleanup, or brain atrophy, in additional embodiments are methods of treating a patient in need of such a therapy with a recombinant LTF-hIgG-Fc fusion protein. In some embodiments are methods of treating a patient in need of such a therapy with a recombinant LTF-hIgG-Fc fusion protein to manage a related neurological deficit, edema, brain cleanup, or brain atrophy. In a preferred embodiment the patient is a companion animal or a human.

In another embodiment, a composition comprising isolated lactoferrin in aqueous solution or powder, wherein the lactoferrin has an ability to prevent, limit or reduce the neurological deficit, edema and brain atrophy caused by ICH in humans is disclosed. In one embodiment, the lactoferrin is human lactoferrin. In another embodiment the lactoferrin is a recombinant human lactoferrin. In a further embodiment, the lactoferrin is fully humanized recombinant human lactoferrin having N-type glycan linked to the polypeptide chain. In a still further embodiment, the recombinant human lactoferrin is expressed in mammalian expression system. In another embodiment, the mammalian expression system is human epithelial kidney cell line. In a further embodiment, the mammalian expression system is Chinese hamster ovary cell line.

In another embodiment, a composition is disclosed comprising an isolated fusion of human lactoferrin with Fc domain for IgG (Fc hLTF), in aqueous solution or powder, wherein the recombinant Fc hLTF has an ability to prevent, limit, or reduce the neurological deficit, edema and brain atrophy caused by ICH in humans. In another embodiment, the recombinant Fc hLTF is a fusion of human lactoferrin and human Fc domain for IgG. In a further embodiment, the recombinant Fc hLTF is expressed in a mammalian expression system. In another embodiment, the mammalian expression system is human epithelial kidney cell line. In a further embodiment, the mammalian expression system is Chinese hamster ovary cell line.

In embodiments described herein, in vitro cell-culture systems and clinically relevant in rodent models of ICH were used to establish that lactoferrin possess biological properties which make it a suitable candidate for treatment of ICH. In some embodiments, LTF effectively combats multifactorial aspects of ICH pathogenesis and it provides a robust protective effect in experimental models of ICH. In additional embodiments, a LTF-hIgG-Fc fusion protein (PRC14) was even more effective than treatment with LTF alone. Thus, in additional embodiments the LTF-hIgG-Fc fusion protein (PRC14) was determined to have extended bioavailability, improved therapeutic efficacy and reduced toxicity as compared to rhLTF alone.

In some embodiments, the present disclosure describes the utility of PRC14—a novel pleotropic fusion protein based on rhLTF and neonatal Fc receptor for IgG—for the treatment of intracranial hemorrhage (ICH).

In some embodiments it is disclosed that LTF possess pleotropic mechanism of action that may effectively combat multifactorial aspects of ICH pathogenesis, in other embodiments LTF provides robust protective effect in experimental models of ICH, and in further embodiments, that an optimized lactoferrin fusion protein comprising the fusion of rhLTF with neonatal Fc receptor for IgG (PRC14) is more effective than LTF alone. The present embodiments may therefore provide several advantages over application of LTF in native form.

In some embodiments, the Fc-fusion protein displays extended plasma half-life, improved stability, improved permeability across biological membranes, including blood-brain-barrier (BBB), cost-effective purification, and may provide preferential targeting of immune cells, as compared to LTF. Thus in some embodiments the Fc-fusion protein provides a method for the management of patients with ICH or ICH related disorder.

In some embodiments disclosed herein, are conserved variants of LTF polypeptides or fusion proteins (such as, but not limited to LTF-hIgG-Fc fusion protein), wherein a "conservative" amino acid substitution refers to the substitution of an amino acid in a polypeptide with another amino acid having similar properties, such as size or charge. In certain embodiments, a polypeptide comprising a conservative amino acid substitution maintains at least one activity of the unsubstituted polypeptide. A conservative amino acid substitution may encompass non-naturally occurring amino acid residues, which are typically incorporated by chemical peptide synthesis rather than by synthesis in biological systems. These include, but are not limited to, peptidomimetics and other reversed or inverted forms of amino acid moieties.

In some embodiments, naturally occurring residues may be divided into classes based on side chain properties: hydrophobic (Met, Ala, Val, Leu, Ile); neutral hydrophilic (Cys, Ser, Thr, Asn, Gln); acidic (Asp, Glu); basic (His, Lys, Arg); residues that influence chain orientation (Gly, Pro); and aromatic (Trp, Tyr, Phe). For example, non-conservative substitutions may involve the exchange of a member of one of these classes for a member from another class.

In making substitutions, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids may be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included.

According to certain embodiments, amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physiochemical or functional properties on such polypeptides.

According to certain embodiments, single or multiple amino acid substitutions (in (conservative amino acid substitutions) may be made in a naturally-occurring sequence and in certain embodiments, in the portion of the polypeptide outside the domain(s) forming intermolecular contacts. In certain embodiments, a conservative amino acid substitution typically may not substantially change the structural characteristics of the reference sequence (e.g., in certain embodiments, a replacement amino acid should not break a helix that occurs in the reference sequence, or disrupt other types of secondary structure that characterizes the reference sequence).

Some embodiments disclose an isolated nucleic acid comprising a nucleotide sequence that encodes a functional domain of LTF or a LTF fusion protein. In some embodiments the isolated nucleic acid encodes at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150, 175, 200, 205, 210, 215, 220, 225, 228, 229, 230, 235, 240 250, 255, 260, 265, 270, 275, 280, 285, 290, 295, 300, 305, 310, 315, 320, 325, 350, 375, 400, 500, 600, 700, 800, 900 or more contiguous amino acids of SEQ ID NO: 2 or fragments thereof. Further, in some embodiments are any range of nucleic acids derivable between any of the above-described integers.

In other embodiments, the present invention provides for an isolated polypeptide or an isolated nucleic acid encoding a polypeptide having in some embodiments between about 70% and about 75%; in further embodiments between about 75% and about 80%; in further still embodiments between about 80% and 90%; or even more further between about 90% and about 99% of amino acids that are identical to (or homologous to) the amino acids of SEQ ID NO: 2 or active fragments thereof.

The percent identity (or homology) is determined herein with regard to the length of the relevant amino acid sequence. Therefore, if a polypeptide of the present invention was comprised within a larger polypeptide, the percent homology is determined with regard only to the portion of the polypeptide that corresponds to the polypeptide of the present invention and not the percent homology of the entirety of the larger polypeptide. "Percent identity" or "% identity," with reference to nucleic acid sequences, refers to the percentage of identical nucleotides between at least two polynucleotide sequences aligned using the Basic Local Alignment Search Tool (BLAST) engine.

In some embodiments, the nucleic acid segments, regardless of the length of the coding sequence itself, may be combined with other DNA sequences, such as promoters, enhancers, polyadenylation signals, additional restriction enzyme sites, multiple cloning sites, other coding segments, and the like. In some embodiments, for example, are recombinant nucleic acids comprising a nucleotide sequence that encode amino acids of SEQ ID NO: 2 or fragments thereof, operably linked to a heterologous promoter.

In certain embodiments the invention provides an isolated nucleic acid obtained by amplification from a template nucleic acid using an appropriate primer that may be used with SEQ ID NO: 1 (the nucleic acid sequence that encoding the lactoferrin fusion protein PRC14).

In some embodiments, a recombinant host cell is disclosed comprising one of the nucleic acid sequences described herein. In some embodiments, a protein composition comprises one of the polypeptides disclosed herein.

In some embodiments, the LTF or LTF-fusion protein has the amino acid sequence of all or part of SEQ ID NO: 2, or a biologically active fragment thereof that retains the biological activity of the LTF or LTF-fusion protein or is a biologically active conservative amino acid substitution variant of SEQ ID NO: 2 or of the fragment.

In some embodiments, the expression vector comprises an AAV viral vector. In some embodiments, the promoter is a constitutive promoter. In some embodiments, the constitutive promoter is a CMV promoter or a hybrid CMV enhancer/chicken β-actin (CAG) promoter. In other embodiments, the promoter is an inducible and/or a cell type-specific promoter.

Amino Acid Sequences: The peptide amino acid sequences that may be used in various embodiments include LTF or LTF-fusion protein (such as but not limited to PRC14) amino acid sequences described herein, as well as analogues and derivatives thereof and functional fragments such as but not limited to the rhodopsin domain. In fact, in some embodiments the any desired peptide amino acid sequences encoded by particular nucleotide sequences may be used, as is the use of any polynucleotide sequences encoding all, or any portion, of desired peptide amino acid sequences. The degenerate nature of the genetic code is well-known, and, accordingly, LTF or LTF-fusion protein (such as but not limited to PRC14) peptide amino acid-encoding nucleotide sequence is generically representative of the well-known nucleic acid "triplet" codon, or in many cases codons, that can encode the amino acid. As such, as disclosed herein, the LTF or LTF-fusion protein (such as but not limited to PRC14) peptide amino acid sequences described herein, when taken together with the genetic code (see, e.g., "Molecular Cell Biology," Table 4-1 at page 109 (Darnell et al., eds., W. H. Freeman & Company, New York, N.Y., 1986)), are generically representative of all the various permutations and combinations of nucleic acid sequences that can encode such amino acid sequences.

Such functionally equivalent peptide amino acid sequences (conservative substitutions) include, but are not limited to, additions or substitutions of amino acid residues within the amino acid sequences encoded by a nucleotide sequence, but that result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example: nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Conservative amino acid substitutions may alternatively be made on the basis of the hydropathic index of amino acids. Each amino acid has been assigned a hydropathic index on the basis of its hydrophobicity and charge characteristics (as described above). They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The use of the hydropathic amino acid index in conferring interactive biological function on a protein is understood in the art (Kyte and Doolittle, J. Mol. Biol. 157:105-132, 1982). It is known that in certain instances, certain amino acids may be substituted for other amino acids having a similar hydropathic index or score and still retain a similar biological activity. In making changes based upon the hydropathic index, in certain embodiments the substitution of amino acids whose hydropathic indices are within ±2 is included, while in other embodiments amino acid substitutions that are within ±1 are included, and in yet other embodiments amino acid substitutions within ±0.5 are included.

In some embodiments, conservative amino acid substitutions may alternatively be made on the basis of hydrophilicity, particularly where the biologically functional protein or peptide thereby created is intended for use in immunological embodiments. In certain embodiments, the greatest local average hydrophilicity of a protein, as governed by the hydrophilicity of its adjacent amino acids, correlates with its immunogenicity and antigenicity, i.e., with a biological property of the protein. The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments the substitution of amino acids whose hydrophilicity values are within ±2 is included, in certain embodiments those that are within ±1 are included, and in certain embodiments those within ±0.5 are included.

Fusion Proteins: The use of fusion proteins in which a polypeptide or peptide, or a truncated or mutant version of peptide is fused to an unrelated protein, polypeptide, or peptide, and may be designed on the basis of the desired peptide encoding nucleic acid and/or amino acid sequences described herein. Such fusion proteins include, but are not limited to: IgG Fc fusions (such as PRC14 as described herein), which stabilize proteins or peptides and prolong half-life in vivo; fusions to any amino acid sequence that allows the fusion protein to be anchored to the cell membrane; or fusions to an enzyme, fluorescent protein, or luminescent protein that provides a marker function.

In certain embodiments, a fusion protein may be purified by utilizing an antibody that selectively binds to the fusion protein being expressed. In alternate embodiments, a fusion protein may be purified by subcloning peptide encoding nucleic acid sequence into a recombination plasmid, or a portion thereof, which is translationally fused to an amino-terminal (N-terminal) or carboxy-terminal (C-terminal) tag consisting of six histidine residues (a "His-tag"; see, e.g., Janknecht et al., Proc. Natl. Acad. Sci. USA 88:8972-8976, 1991). Extracts from cells expressing such a construct are loaded onto $Ni^{2+}$ nitriloacetic acid-agarose columns, and histidine-tagged proteins are selectively eluted with imidazole-containing buffers.

Recombinant Expression: While in some embodiments peptide amino acid sequences described may be chemically synthesized, large polypeptides sequences may be produced by recombinant DNA technology using techniques well-known in the art for expressing nucleic acids containing a nucleic acid sequence that encodes the desired peptide. Such methods may be used to construct expression vectors containing peptide encoding nucleotide sequences and appropriate transcriptional and translational control signals. These methods include, for example, in vitro recombinant DNA techniques, synthetic techniques, and in vivo genetic recombination (see, e.g., "Molecular Cloning, A Laboratory Manual," supra, and "Current Protocols in Molecular Biology," supra). Alternatively, in some embodiments RNA and/or DNA encoding desired peptide encoding nucleotide sequences may be chemically synthesized using, for example, synthesizers (see, e.g., "Oligonucleotide Synthesis: A Practical Approach" (Gait, ed., IRL Press, Oxford, United Kingdom, 1984)).

In some embodiments, a variety of host-expression vector systems may be utilized to express peptide encoding nucleotide sequences. When the desired peptide or polypeptide is soluble or a soluble derivative, the peptide or polypeptide may be recovered from the host cell culture, i.e., from the host cell in cases where the peptide or polypeptide is not secreted, and from the culture media in cases where the peptide or polypeptide is secreted by the host cell. However, suitable expression systems also encompass engineered host cells that express the desired polypeptide or functional equivalents anchored in the cell membrane. Purification or enrichment of the desired peptide from such expression systems may be accomplished using appropriate detergents and lipid micelles, and methods well-known to those skilled in the art. Furthermore, such engineered host cells themselves may be used in situations where it is desired not only to retain the structural and functional characteristics of the peptide, but to assess biological activity, e.g., in certain drug screening assays.

In certain applications, transient expression systems are desired. However, for long-term, high-yield production of recombinant proteins or peptides, stable expression is generally preferred. For example, cell lines that stably express the desired protein, polypeptide, peptide, or fusion protein may be engineered. Rather than using expression vectors that contain viral origins of replication, in some embodiments host cells may be transformed with DNA controlled by appropriate expression control elements (e.g., promoter, enhancer sequences, transcription terminators, polyadenylation sites, etc.), and a selectable marker. In some embodiments, following the introduction of the foreign DNA, engineered cells may be allowed to grow for about 1-2 days in an enriched media, and then switched to a selective media. The selectable marker in the recombinant plasmid confers resistance to the selection, and allows cells to stably integrate the plasmid into their chromosomes and grow to form foci, which in turn may be cloned and expanded into cell lines. This method may be used to engineer cell lines that express the desired gene products or portions thereof. Such engineered cell lines may be particularly useful in screening and evaluation of compounds that affect the endogenous activity of a desired protein, polypeptide or peptide.

A number of selection systems may be used, including, but not limited to, the herpes simplex virus thymidine kinase (Wigler et al., Cell 11:223-232, 1977), hypoxanthine-guanine phosphoribosyltransferase (Szybalska and Szybalski, Proc. Natl. Acad. Sci. USA 48:2026-2034, 1962), and adenine phosphoribosyltransferase (Lowy et al., Cell 22:817-823, 1980) genes, which may be employed in tk-, hgprt- or aprt-cells, respectively. Anti-metabolite resistance can also be used as the basis of selection for the following genes: dihydrofolate reductase (dhfr), which confers resistance to methotrexate (Wigler et al., Proc. Natl. Acad. Sci. USA 77:3567-3570, 1980, and O'Hare et al., Proc. Natl. Acad. Sci. USA 78:1527-1531, 1981); guanine phosphoribosyl transferase (gpt), which confers resistance to mycophenolic acid (Mulligan and Berg, Proc. Natl. Acad. Sci. USA 78:2072-2076, 1981); neomycin phosphotransferase (neo), which confers resistance to the aminoglycoside G-418 (Colbere-Garapin et al., J. Mol. Biol. 150:1-14, 1981); and hygromycin B phosphotransferase (hpt), which confers resistance to hygromycin (Santerre et al., Gene 30:147-156, 1984).

In some embodiments, host cells/expression systems that may be used for purpose of providing compositions to be used in the disclosed methods include, but are not limited to, microorganisms such as bacteria (e.g., *E. coli, B. subtilis*) transformed with a recombinant bacteriophage DNA, plasmid DNA, or cosmid DNA expression vector containing a desired peptide encoding nucleotide sequence; yeast (e.g., *Saccharomyces cerevisiae, Pichia pastoris*) transformed with a recombinant yeast expression vector containing a desired peptide encoding nucleotide sequence; insect cell systems infected with a recombinant virus expression vector (e.g., baculovirus) containing a desired peptide encoding nucleotide sequence; plant cell systems infected with a recombinant virus expression vector (e.g., cauliflower mosaic virus, CaMV; tobacco mosaic virus, TMV), or transformed with a recombinant plasmid expression vector (e.g., Ti plasmid), containing a desired peptide encoding nucleotide sequence; or mammalian cell systems (e.g., COS, CHO, BHK, 293, 3T3) harboring a recombinant expression construct containing a desired peptide encoding nucleotide sequence and a promoter derived from the genome of mammalian cells (e.g., metallothionein promoter) or from mammalian viruses (e.g., the adenovirus late promoter, the vaccinia virus 7.5K promoter).

In some embodiments, bacterial systems and a number of different expression vectors may be advantageously selected depending upon the use intended for the desired gene product being expressed. For example, when a large quantity of such a protein is to be produced, such as for the generation of pharmaceutical compositions comprising a desired peptide, or for raising antibodies to the protein, vectors that direct the expression of high levels of fusion protein products that are readily purified may be desirable. Such vectors include, but are not limited to: the *E. coli* expression vector pUR278 (Ruther and Müller-Hill, EMBO J. 2:1791-1794, 1983), in which a peptide encoding sequence may be ligated individually into the vector in frame with the lacZ coding region so that a fusion protein is produced; pIN vectors (Inouye and Inouye, Nucleic Acids Res. 13:3101-3110, 1985, and Van Heeke and Schuster, J. Biol. Chem. 264:5503-5509, 1989); and the like. pGEX vectors (GE Healthcare, Piscataway, N.J.) may also be used to express a desired peptide moiety as a fusion protein with glutathione S-transferase (GST). In general, such fusion proteins are soluble and can easily be purified from lysed cells by adsorption to glutathione-agarose beads, followed by elution in the presence of free glutathione. The pGEX vectors are designed to include thrombin or factor Xa protease cleavage sites so that the cloned desired peptide encoding gene product may be released from the GST moiety.

In some embodiments an exemplary insect system such as *Autographa californica* nuclear polyhedrosis virus (AcNPV) is disclosed and used as a vector to express a desired peptide encoding sequence. The virus grows in *Spodoptera frugiperda* cells. A desired peptide encoding sequence may be cloned individually into a non-essential region (for example the polyhedrin gene) of the virus, and placed under control of an AcNPV promoter (for example the polyhedrin promoter). Successful insertion of a desired peptide encoding sequence will result in inactivation of the polyhedrin gene and production of non-occluded recombinant virus (i.e., virus lacking the proteinaceous coat coded for by the polyhedrin gene). The recombinant viruses are then used to infect *Spodoptera frugiperda* cells in which the inserted polynucleotide is expressed (see, e.g., Smith et al., J. Virol. 46:584-593, 1983, and U.S. Pat. No. 4,215,051).

In some embodiments a number of viral-based expression systems may be utilized in mammalian host cells. In cases where an adenovirus is used as an expression vector, a desired peptide encoding nucleotide sequence may be ligated to an adenovirus transcription/translation control complex, e.g., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing desired peptide products in infected hosts (see, e.g., Logan and Shenk, Proc. Natl. Acad. Sci. USA 81:3655-3659, 1984). Specific initiation signals may also be required for efficient translation of inserted desired peptide encoding nucleotide sequences. These signals include the ATG initiation codon and adjacent sequences. In some cases exogenous translational control signals, including, perhaps, the ATG initiation codon, may be provided. Furthermore, the initiation codon should be in phase with the reading frame of the desired peptide encoding coding sequence to ensure translation of the entire insert. These exogenous translational control signals and initiation codons may be of a variety of origins, both natural and synthetic. The efficiency of expression may be enhanced by the inclusion of appropriate transcription enhancer elements, transcription terminators, etc. (see, e.g., Nevins, CRC Crit. Rev. Biochem. 19:307-322, 1986), and in some embodiments, in yeast, a number of vectors containing constitutive or inducible promoters may be used.

In some embodiments in plants, a variety of different plant expression vectors may be used, and expression of a desired peptide encoding sequence may be driven by any of a number of promoters. For example, viral promoters such as the 35S RNA or 19S RNA promoters of CaMV (Brisson et al., Nature 310:511-514, 1984), or the coat protein promoter of TMV (Takamatsu et al., EMBO J. 6:307-311, 1987) may be used. Alternatively, plant promoters such as the promoter of the small subunit of RUBISCO (Coruzzi et al., EMBO J. 3:1671-1679, 1984, and Broglie et al., Science 224:838-843, 1984), or heat shock promoters, e.g., soybean hsp17.5-E or hsp17.3-B (Gurley et al., Mol. Cell. Biol. 6:559-565, 1986) may be used. These constructs may be introduced into plant cells using, for example, Ti plasmids, Ri plasmids, plant virus vectors, direct DNA transformation, microinjection, or electroporation.

In other embodiments, a host cell strain may be chosen that modulates the expression of the inserted desired peptide encoding sequence, or modifies and processes the desired peptide encoding nucleic acid sequence in a desired fashion. Such modifications (e.g., glycosylation) and processing (e.g., cleavage) of protein products may affect certain functions of the protein. Different host cells have characteristic and specific mechanisms for post-translational processing and modification of proteins and peptides. Appropriate cell lines or host systems may be chosen to ensure the correct or desired modification and processing of the desired protein, polypeptide, or peptide expressed. To this end, eukaryotic host cells that possess the cellular machinery for desired processing of the primary transcript, and glycosylation and/or phosphorylation of desired peptide encoding nucleic acid sequence be used. Such mammalian host cells include, but are not limited to, Chinese hamster ovary (CHO), VERO, baby hamster kidney (BHK), HeLa, monkey kidney (COS), MDCK, 293, 3T3, WI38, human hepatocellular carcinoma (e.g., Hep G2), and U937 cells.

Compositions as Therapeutics: The use of LTF or LTF-fusion protein (such as but not limited to PRC14), or active fragments thereof may be used as therapeutics. In certain embodiments the presently disclosed compositions may be used to improve symptoms associated with ICH or related disorders, as well as may be used to aid in diagnosis, prevention, and/or treatment of intracranial hemorrhage (ICH) or ICH related disorders. In certain embodiments the presently disclosed compositions may be administered in combination with one or more additional compounds or agents ("additional active agents") for the treatment, management, and/or prevention of among other things intracranial hemorrhage (ICH) or ICH related disorders, and as therapy for such disorders and their symptoms. Such therapies may be administered to a patient at therapeutically effective doses to treat or ameliorate, intracranial hemorrhage (ICH) or ICH related disorders and as therapy for such disorders. A therapeutically effective dose refers to that amount of the compound sufficient to result in any delay in onset, amelioration, or retardation of disease symptoms.

In other embodiments, toxicity and therapeutic efficacy of such compositions may be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index, expressed as the ratio LD50/ED50. Compositions that exhibit large therapeutic indices are preferred. Compounds that exhibit toxic side effects may be used in certain embodiments, however, care should usually be taken to design delivery systems that target such compositions preferentially to the site of affected tissue, in order to minimize potential damage to uninfected cells and, thereby, reduce side effects.

In some embodiments the data obtained from cell culture assays and animal studies disclosed herein may be used in formulating a range of dosages for use in humans. The dosages of such compositions lie preferably within a range of circulating concentrations that include the ED50 with little or no toxicity. The dosage may vary within this range depending on the dosage form employed and the route of administration utilized. For any composition, the therapeutically effective dose may be estimated initially from cell culture assays. A dose may be formulated in animal models to achieve a circulating plasma concentration range that includes the IC50 (i.e., the concentration of the test composition that achieves a half-maximal inhibition of symptoms) as determined in cell culture. Such information may be used to more accurately determine useful doses in humans. Plasma levels may be measured, for example, by high performance liquid chromatography.

In some embodiments, when the therapeutic treatment of among other things intracranial hemorrhage (ICH) or ICH related disorders and as therapy for such disorders is considered, the appropriate dosage may also be determined using animal studies to determine the maximal tolerable dose, or MTD, of a bioactive agent per kilogram weight of the test subject. In general, at least one animal species tested is mammalian.

Additionally, in some embodiments, the bioactive agent may be coupled or complexed with a variety of well-established compositions or structures that, for instance, enhance the stability of the bioactive agent, or otherwise enhance its pharmacological properties (e.g., increase in vivo half-life, reduce toxicity, etc.).

Such therapeutic agents may be administered by any number of methods known to those of ordinary skill in the art including, but not limited to, inhalation, subcutaneous (sub-q), intravenous (i.v.), intranasal (i.n.), intraperitoneal (i.p.), intramuscular (i.m.), or intrathecal injection, or topically applied (transderm, ointments, creams, salves, eye drops, and the like), as described in greater detail below.

Pharmaceutical Compositions: Pharmaceutical compositions for use in accordance with the presently described compositions may be formulated in conventional manners using one or more physiologically acceptable carriers or excipients.

In some embodiments, pharmaceutical compositions can comprise formulation materials for modifying, maintaining, or preserving, for example, the pH, osmolarity, viscosity, clarity, color, isotonicity, odor, sterility, stability, rate of dissolution or release, adsorption or penetration of the composition. Suitable formulation materials include, but are not limited to: amino acids (for example, glycine, glutamine, asparagine, arginine and lysine); antimicrobials; antioxidants (for example, ascorbic acid, sodium sulfite and sodium hydrogen-sulfite); buffers (for example, borate, bicarbonate, Tris-HCl, citrates, phosphates and other organic acids); bulking agents (for example, mannitol and glycine); chelating agents (for example, ethylenediamine tetraacetic acid (EDTA)); complexing agents (for example, caffeine, polyvinylpyrrolidone, beta-cyclodextrin, and hydroxypropyl-beta-cyclodextrin); fillers; monosaccharides, disaccharides, and other carbohydrates (for example, glucose, mannose and dextrins); proteins (for example, serum albumin, gelatin and immunoglobulins); coloring, flavoring, and diluting agents; emulsifying agents; hydrophilic polymers (for example, polyvinylpyrrolidone); low molecular weight polypeptides; salt-forming counterions (for example, sodium); preservatives (for example, benzalkonium chloride, benzoic acid, salicylic acid, thimerosal, phenethyl alcohol, methylparaben, propylparaben, chlorhexidine, sorbic acid and hydrogen peroxide); solvents (for example, glycerin, propylene glycol and polyethylene glycol); sugar alcohols (for example, mannitol and sorbitol); suspending agents; surfactants or wetting agents (for example, pluronics, PEG, sorbitan esters, polysorbates (for example, polysorbate 20 and polysorbate 80), triton, tromethamine, lecithin, cholesterol, and tyloxapal); stability enhancing agents (for example, sucrose and sorbitol); tonicity enhancing agents (for example, alkali metal halides (for example, sodium or potassium chloride), mannitol, and sorbitol); delivery vehicles; diluents; excipients; and pharmaceutical adjuvants.

Additionally, in some embodiments the described therapeutic peptides may be linked to a half-life extending vehicle. Certain exemplary half-life extending vehicles are known in the art, and include, but are not limited to, the Fc domain, polyethylene glycol, and dextran (see, e.g., PCT Patent Application Publication No. WO 99/25044).

In other embodiments, these agents may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a sui vehicle, e.g., sterile pyrogen-free water, before use.

In some embodiments, the agents may also be formulated as compositions for rectal administration such as suppositories or retention enemas, e.g., containing conventional suppository bases such as cocoa butter or other glycerides.

In addition to the formulations described previously, the agents may also be formulated as a depot preparation. Such long acting formulations may be administered by implantation (for example subcutaneously or intramuscularly) or by intramuscular injection. For example, agents may be formulated with suitable polymeric or hydrophobic materials (for example as an emulsion in an acceptable oil), ion exchange resins, or as sparingly soluble derivatives, for example, as a sparingly soluble salt. The compositions may, if desired, be presented in a pack or dispenser device, which may contain one or more unit dosage forms containing the active ingredient. The pack may for example comprise metal or plastic foil, such as a blister pack. The pack or dispenser device may be accompanied by instructions for administration.

Active compositions may be administered by controlled release means or by delivery devices that are well-known to those of ordinary skill in the art. Such dosage forms may be used to provide slow or controlled-release of one or more active ingredients using, for example, hydropropylmethyl cellulose, other polymer matrices, gels, permeable membranes, osmotic systems, multilayer coatings, microparticles, liposomes, microspheres PEG or a combination thereof, to provide the desired release profile in varying proportions. Exemplary sustained release matrices include, but are not limited to, polyesters, hydrogels, polylactides, copolymers of L-glutamic acid and gamma ethyl-L-glutamate, poly (2-hydroxyethyl-methacrylate), ethylene vinyl acetate (Langer et al., supra), and poly-D(−)-3-hydroxybutyric acid. Sustained release compositions may include liposomes, which may be prepared by any of several methods known in the art. Suitable controlled-release formulations known to those of ordinary skill in the art, including those described herein, may be readily selected for use with the presently disclosed compositions. Certain embodiments encompass single unit dosage forms suitable for oral administration such as, but not limited to, tablets, capsules, gelcaps, and caplets that are adapted for controlled-release.

In some cases, active ingredients of the disclosed methods and compositions are preferably not administered to a patient at the same time or by the same route of administration. Therefore, in some embodiments are kits that, when used by the medical practitioner, can simplify the administration of appropriate amounts of active ingredients to a patient.

In some embodiments, a typical kit comprises a single unit dosage form of one or more of the therapeutic agents disclosed, alone or in combination with a single unit dosage form of another agent that may be used in combination with the disclosed compositions. Disclosed kits can further comprise devices that are used to administer the active ingredients. Examples of such devices include, but are not limited to, syringes, drip bags, patches, and inhalers.

Disclosed kits can further comprise pharmaceutically acceptable vehicles that may be used to administer one or more active ingredients. For example, if an active ingredient is provided in a solid form that must be reconstituted for parenteral administration, the kit can comprise a sealed container of a suitable vehicle in which the active ingredient may be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. However, in specific embodiments, the disclosed formulations do not contain any alcohols or other co-solvents, oils or proteins.

Nucleic Acid Sequences: LTF or LTF-fusion protein nucleic acid sequences for use in the disclosed methods and compositions the active portion of the presently disclosed LTF or LTF-fusion protein such as but not limited to the nucleic acid sequences that encode PRC14 (SEQ ID NO: 1; and SEQ ID NO: 2).

In some embodiments, the use of an active portion of a presently disclosed LTF or LTF-fusion protein, such as, but not limited to PRC14, includes all or portions of the sequences described herein (and expression vectors comprising the same), and additionally the use of any nucleotide sequence encoding a contiguous an active portion of the presently disclosed LTF or LTF-fusion protein, such as, but not limited to PRC14, open reading frame (ORF) that hybridizes to a complement of a LTF or LTF-fusion protein, such as, but not limited to PRC14 described herein under highly stringent conditions, e.g., hybridization to filter-bound DNA in 0.5 M NaHPO4, 7% sodium dodecyl sulfate (SDS), 1 mM EDTA at 65° C., and washing in 0.1×SSC/0.1% SDS at 68° C. ("Current Protocols in Molecular Biology," Vol. 1 and 2 (Ausubel et al., eds., Green Publishing Associates, Incorporated, and John Wiley & Sons, Incorporated, New York, N.Y., 1989)), and encodes a functionally equivalent LTF or LTF-fusion protein, (or active portion thereof) gene product or the active portion thereof. Additionally disclosed is the use of any nucleotide sequence that hybridizes to the complement of a DNA sequence that encodes a LTF or LTF-fusion protein amino acid sequence under moderately stringent conditions, e.g., washing in 0.2×SSC/0.1% SDS at 42° C. ("Current Protocols in Molecular Biology," supra), yet still encodes a functionally equivalent LTF or LTF-fusion protein product. Functional equivalents of LTF or LTF-fusion protein include, but are not limited to, naturally occurring versions of LTF or LTF-fusion protein present in other species (orthologs and homologs), and mutant versions of LTF or LTF-fusion protein, whether naturally occurring or engineered (by site directed mutagenesis, gene shuffling, or directed evolution, as described in, for example, U.S. Pat. No. 5,837,458) or active portion thereof. The disclosure also includes the use of degenerate nucleic acid variants (due to the redundancy of the genetic code) of the identified LTF or LTF-fusion protein polynucleotide sequences.

Additionally disclosed is the use of polynucleotides encoding LTF or LTF-fusion protein ORFs, or their functional equivalents, encoded by polynucleotide sequences that are about 99, 95, 90, or about 85 percent similar to the corresponding regions of the LTF or LTF-fusion protein sequences described herein (as measured by BLAST sequence comparison analysis using, for example, the University of Wisconsin GCG sequence analysis package (SEQUENCHER 3.0, Gene Codes Corporation, Ann Arbor, Mich.) using default parameters).

In certain embodiments, the invention comprises isolated nucleic acid segments and recombinant vectors which encode a protein or peptide that includes within its amino acid sequence an amino acid sequence of a LTF or LTF-fusion protein or a functional portions or variant thereof, such as those identified and cloned, such as, but not limited to PRC14 (SEQ ID NO: 2). In some embodiments, a portion of a LTF or LTF-fusion protein and has relatively few amino acids which are not identical to, or a biologically functional equivalent of, the amino acids of the full-length LTF or LTF-fusion protein. The term "functional equivalent" is well understood in the art. Accordingly, sequences which have between about 70% and about 80%; or more preferably, between about 85% and about 90%; or even more preferably, between about 90 and 95% and about 99%; of amino acids which are identical or functionally equivalent to the amino acids of the identified and cloned LTF or LTF-fusion protein, such as but not limited to PRC14 (SEQ ID NO: 2).

The nucleic acid segments of the present invention, regardless of the length of the coding sequence itself, may be combined with other sequences, such as promoters, polyadenylation signals, additional restriction enzyme sites, multiple cloning sites, other coding segments, and the like, such that their overall length may vary considerably. It is therefore disclosed that a nucleic acid fragment of almost any length may be employed, with the total length preferably being limited by the ease of preparation and use in the intended recombinant DNA protocol. For example, nucleic acid fragments may be prepared which include a short stretch complementary to nucleic acids that encode the polypeptides of SEQ ID NO: 2, such as about 10 to 15 or 20, 30, or 40 or 50 or 100 or 200 or 300 or 400 or 500 or 600 so nucleotides, and which are up to or so base pairs in length. DNA segments with total lengths of about 2837, 2500, 2000, 1000, 500, 200, 100 and about 50 base pairs in length are also disclosed to be useful.

In some embodiments, isolated nucleic acids that encode the amino acids of a LTF or LTF-fusion protein or fragment thereof and recombinant vectors incorporating nucleic acid sequences which encode a LTF or LTF-fusion protein or peptide and that includes within its amino acid sequence an amino acid sequence in accordance with SEQ ID NO: 2. In some embodiments, a purified nucleic acid segment that encodes a protein that encodes a LTF or LTF-fusion protein or fragment thereof, the recombinant vector may be further defined as an expression vector comprising a promoter operatively linked to the LTF or LTF-fusion protein-encoding nucleic acid segment.

In additional embodiments, is a host cell, made recombinant with a recombinant vector comprising LTF or LTF-fusion protein-encoding nucleic acid segments. The recombinant host cell may be a prokaryotic cell or a eukaryotic cell. As used herein, the term "engineered" or "recombinant" cell is intended to refer to a cell into which a recombinant gene, such as a gene encoding a LTF or LTF-fusion protein, has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a copy of a genomic gene or a cDNA gene, or will include genes positioned adjacent to a promoter not naturally associated with the particular introduced gene. In some embodiments, nucleic acid molecules having sequence regions consisting of contiguous nucleotide stretches of about 14, 15-20, 30, 40, 50, or even of about 100 to about 200 nucleotides or so, identical or complementary to the LTF or LTF-fusion protein-encoding nucleic acid sequences. Without further elaboration, it is believed that one skilled in the art can, using the description herein, could utilize the present invention to its fullest extent. The embodiments described herein are to be construed as illustrative and not as constraining the remainder of the disclosure in any way whatsoever. For example, although the described embodiments illustrate use of the present compositions and methods on laboratory animals, those of skill in the art would readily recognize that these methods and compositions could also be applied to both human and veterinary medicine.

The following Examples section provides further details regarding examples of various embodiments. It should be appreciated by those of skill in the art that the techniques disclosed in the examples that follow represent techniques and/or compositions discovered by the inventors to function well. However, those of skill in the art should, in light of the present disclosure, appreciate that many changes may be made in the specific embodiments which are disclosed and still obtain a like or similar result without departing from the spirit and scope of the invention. These examples are illustrations of the methods and systems described herein and are not intended to limit the scope of the invention. Non-limiting examples of such include, but are not limited to those presented below.

EXAMPLES

Example 1

Production and purification of lactoferrin-higg2-fc fusion protein (LTF-hIgG2-Fc: PRC14): The production of human LTF-human IgG2 Fc fusion protein (LTF-hIgG2-Fc) in CHO DG44 cells using serum free medium, followed by two-step purification, endotoxin removal and lyophilization. Construction of LTF-fusion protein (PRC14): A LTF-hIgG2-Fc fusion construct was generated through overlap PCR and further subcloned into a stable expression plasmid for transfection of CHO-DG44 cells using Freestyle max reagent (Invitrogen, Cat. No 16447, CA USA) (FIG. 1). The transfected CHO-DG44 cells were cultured in 96-well plates with methionine sulphoximine (MSX) selection medium, and the best expressing clone was expanded to 24-well plates, T-25 flask and finally scale up into shaker flask system for production of initial quantities of the LTF-hIgG2-Fc fusion protein. The media, containing LTF-IgG Fc fusion protein, was harvested, centrifuged and then applied to Mabselect Sure (GE) protein-A affinity column for purification. The enriched LTF-hIgG2-Fc fusion protein was further purified on a cation exchange column at proprietary buffer conditions. The Endotoxin Removal Resin (ToxinEraser™) was used for final purification of the pilot batch of PRC14 (LTF-hIgG2-Fc). A more detailed description of this construction appears in the paragraphs below.

Figure 2:
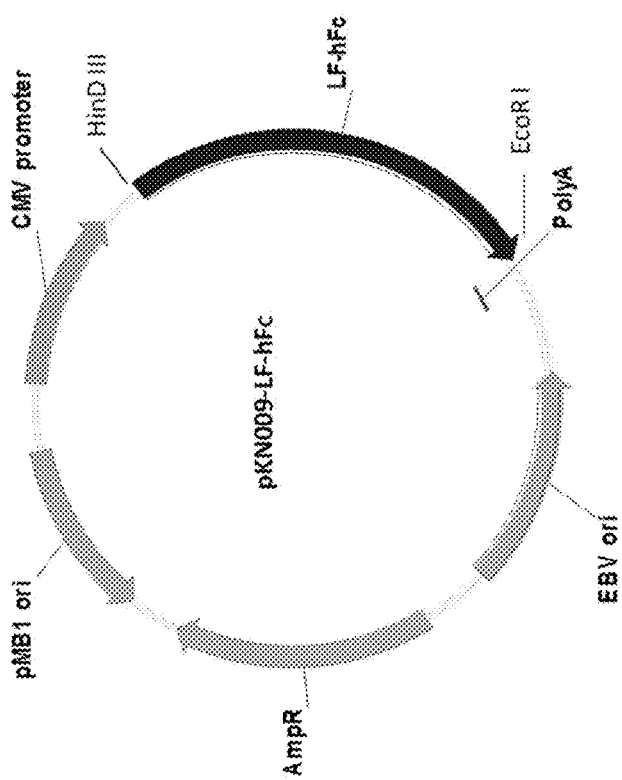
FIG. 2 depicts a map of pKN009-LF-hFc expression vector. The DNA sequence of the lactoferrin-hIgG2-Fc fusion protein has been incorporated under the control of a CMV promoter using the Hind III and EcoR I sites.

Plasmid Construction: LTF-hIgG2-Fc fusion gene was generated through overlap PCR and further subcloned into pUC57 using EcoRI and HindIII (FIG. 1) to generate pKN009-LTF-hFc. expression plasmid (FIG. 2). The resulting nucleic acid sequence (SEQ ID NO: 1) which includes the nucleic acid sequences for cloning into the vector (which appear in the enlarged bolded font). The amino acid sequence (SEQ ID NO: 2) The mammalian expression plasmids containing LTF-hIgG2-Fc sequence were extracted and further ethanol precipitated for DNA lipotransfection.

Figure 3:
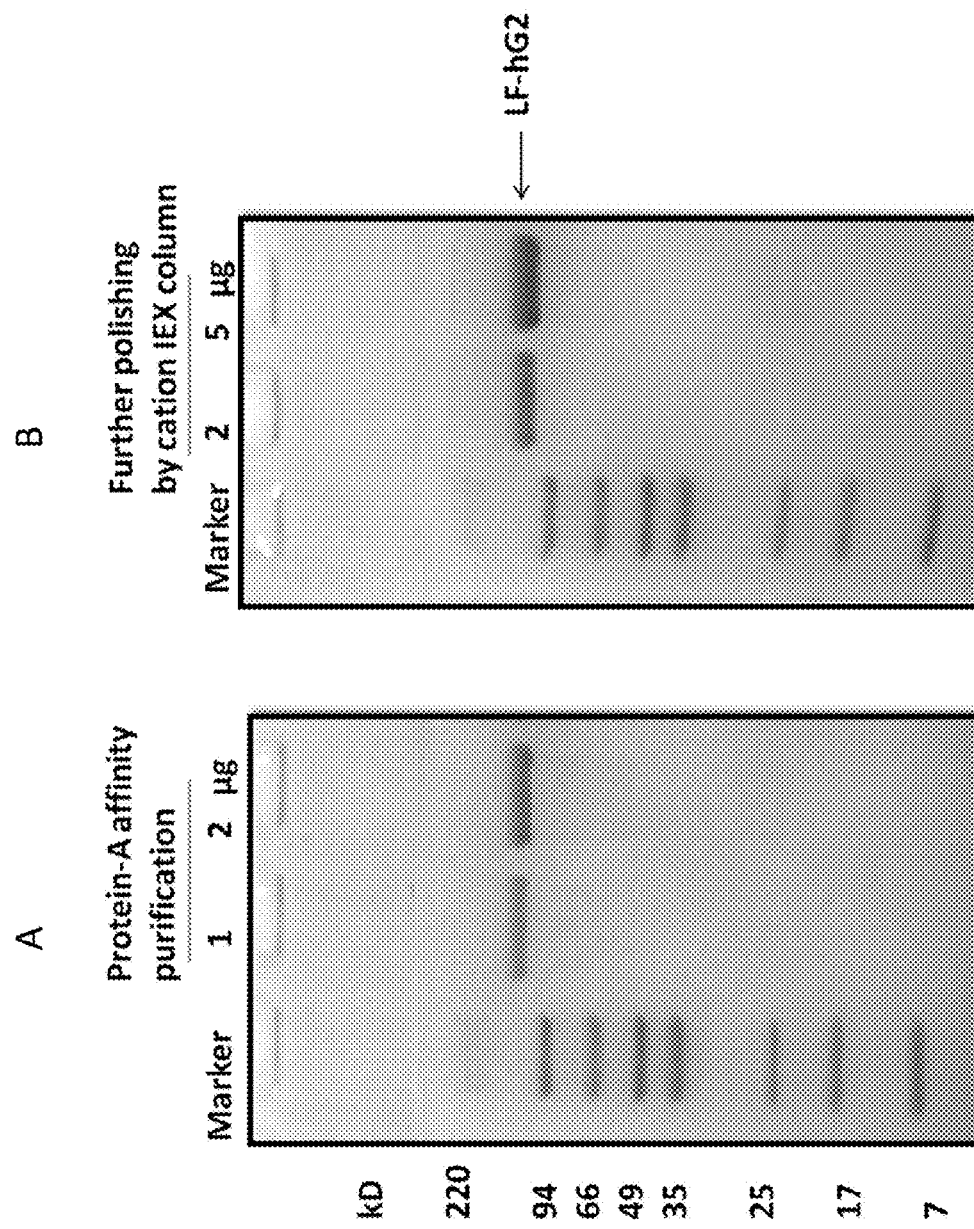
FIG. 3 depicts an SDS PAGE of purified lactoferrin-hIgG2-Fc fusion protein (PRC14: LF-hG2). The final product is near homogenous by SDS PAGE and shows approximate molecular weight at 120 kD.

Protein expression: To produce fusion protein, cells obtained from a stable pool of CHO-DG44 cells were transfected with the expression plasmid pKN009-LF-hFc (FIG. 2) using Freestyle max reagent (Cat. No 16447, Invitrogen™, Grand Island, N.Y., USA). Transfected CHO-DG44 cells were cultured in 96-well plates with MSX selection medium, and three weeks later the wells was screened using SDS-PAGE to identify those expressing lactoferrin-hIgG2-Fc fusion protein (FIG. 3). The best clones were expanded first into 24-well plates, then into T-25 flasks and finally scaled up into shaker flask system for production of fusion protein. The culture medium was CD CHO medium (Invitrogen™ Grand Island, N.Y., USA), a protein-free, serum-free, chemically-defined medium optimized for the growth of CHO cells and expression of recombinant proteins in suspension culture.

Figure 4:
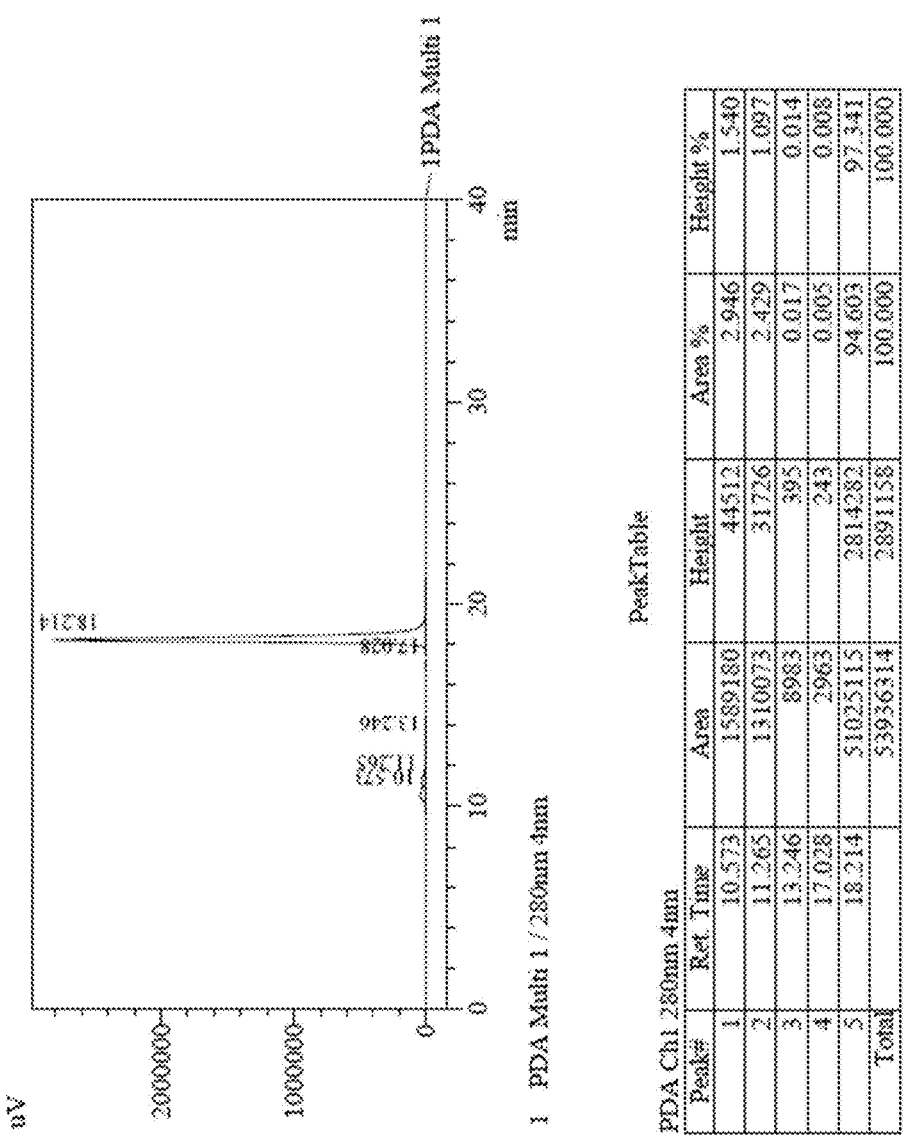
FIG. 4 depicts a HPLC analysis which demonstrates that the purity of lactoferrin-hIgG2 Fc fusion protein was greater than 97%.
Figure 5:
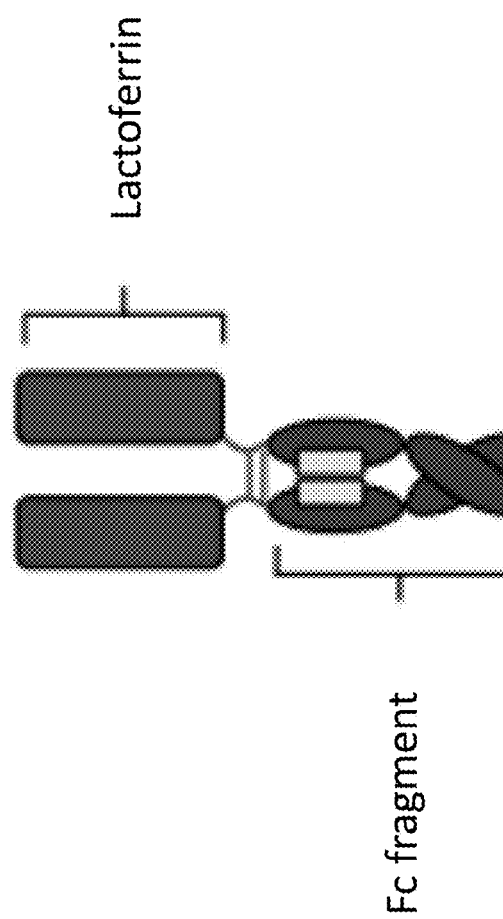
FIG. 5 is a drawing of a lactoferrin-hIgG2-Fc fusion protein such as PRC14.

Protein purification: The supernatants harvest was first 10,000 rpm centrifuged to remove cell debris and then applied to MabSelect™ SuRe™ (GE Healthcare Bio-Sciences, Pittsburgh, Pa., USA) protein-A affinity column for purification (FIG. 3, PANEL A), after which the enriched LTF-hIgG2-Fc fusion protein was placed into to a low salt 0.1M NaAc (pH 5.5) buffer, and loaded to a cation exchange column (TOSOH: TOYOPEARL GigaCap S-650M) for further purification (FIG. 3, panel B). After loading and balancing in 0.1M NaAc (pH 5.5), the LTF-hIgG2-Fc fusion protein was eluted by PB buffer with 1M NaCl with 5% Tehalose. The fusion protein was diluted 5 fold in PBS (0.15M NaCl, 5% Tehalose), and after cation exchange chromatography, the purified Ab was applied to the high capacity endotoxin removal affinity resin column (Catalog no: 88270; Thermo Scientific Pierce, Grand Island, N.Y., USA) and the flow through was adjusted to 2.5 mg/ml for final lyophilization (as calculated using a lactoferrin hypothetic UV280 molar extinction coefficient of 1.15). HPLC analysis demonstrated that the purity of LTF-hIgG2-Fc fusion protein was greater than 97% (FIG. 4).

Endotoxin analysis: To determine if there was endotoxin present in the purified products, the FDA approved Pyrosate® Kit (#PSD10, sensitivity 0.25 EU/ml) Rapid Endotoxin Detection (Associates of Cape Cod, Inc., East Falmouth, Mass., USA) was used as directed by the manufacture. The purified fusion protein was adjusted to 0.25 mg/ml with endotoxin-free water and the PSD10 kit was utilized to determine if endotoxin was present. It was determined that there was less than 1 EU/mL of endotoxin present in the purified fusion protein preparations.

Example 2

Figure 6:
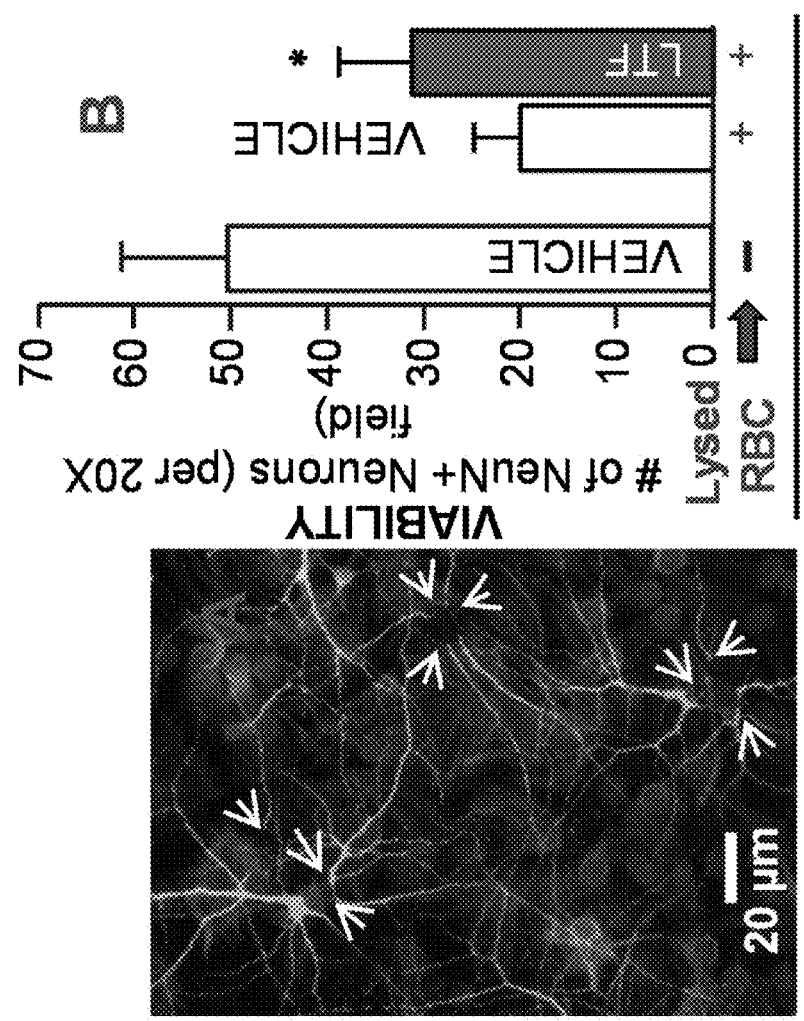
FIG. 6 depicts an immunohistochemical stain of neuronal cells. Panel A: MAP2-labeled neurons (green) and GFAP-labeled astrocytes (red) in the primary neuron-glia co-cultures at 24 h after exposure to RBC-lysate. Arrows indicate the swollen and broken soma and dendrites. Astrocytes are less susceptible to the injury. Panel B: The number of the surviving NeuN+-neurons in the neuron-glia cultures at 24 h after exposure to lysed RBC with or without LTF. Data are mean±SEM (n=15).*p≤0.05.

In vitro evidence supporting the use of lactoferrin to treat intracerebral hemorrhage (ICH) related symptoms. To establish the ability of rhLTF to enhance brain cell survival in response to hemolytic product, an in vitro "ICH-like" injury model was utilized. This model is based on adding RBC-lysate to the primary neuronal-glial co-cultures (a mixed brain cell culture consisting of neurons, astrocytes, oligodendrocytes and microglia). As expected, RBC-lysate caused an injury to neurons (swelling of the soma and dendrites, followed by lyses) and remarkably it was determined that physiologically relevant concentration of LTF (rhLTF) (10 µg/ml) strongly reduced the neuronal damage caused by hemolysates (more NeuN-positive cells survived) (as shown in FIG. 6).

To characterize the effect of LTF on the function and phenotype of microglia/macrophage (MMΦ), rhLTF was added to the cultured rat primary MMΦ with or without ANs (apoptotic PMNs; target of efferocytosis-phagocytosis of apoptotic cells), and assessed the effect of rhLTF on the efferocytosis process. ANs were produced by subjecting the freshly isolated blood PMN to 43° C. for 1 h and then incubated at 37° C. in 5% CO2 incubator for 16 h—this resulted in the death of more than 95% of the PMNs via apoptosis, and these ANs no longer contained LTF. It was determined that MMΦ are capable of phagocytosing the ANs and that rhLTF, 1-100 μg/ml augments this process in a dose-dependent fashion. The results from treatment with 10 μg/kg is shown in FIG. 7 and demonstrates that LTF augments ANs engulfment. This lactoferrin-mediated phagocytosis coincided with the following changes of mRNA expression in the MMΦ: (1) increase in the scavenger receptors (e.g., CD91, CD36—important mediators of the brain cleanup process), (2) increase in nuclear factor-erythroid E2-related factor 2 (Nrf2), (3) increase in anti-inflammatory factors (arginase-1, IL-1Ra and TGFβ), and (4) decrease in pro-inflammatory factors (TNFα, IL-1β, NOX1 and MMP9). This gene profile overall typifies MMΦ polarization toward the "healing" M2-like phenotype that is known to play important role in the tissue repair process. Thus, LTF can induce differentiation of MMΦ into pro-phagocytotic and anti-inflammatory M2 phenotype. Nrf2 is a transcription factor and master regulator of the antioxidant and detoxification responses that are critical for self-protection, protection of other cells, and the clearance function of MMΦ upon exposure to an "inflamed" environment.

Example 3

Treatment with LTF. Autologous blood injection model of ICH in rodents: A clinically-relevant ICH model in mouse that is based on intra-striatal injection of autologous blood (see for example 71, 72, 79). In summary, randomly selected male mice (weighing~30 g) under isoflurane anesthesia were immobilized onto a stereotaxic frame. A burr hole was drilled in the skull and a 31 gauge steel cannula was inserted for the whole fresh blood (12 μl; from the femoral artery) infusion. The core body temperature was maintained at 37±0.5° C. during surgery and the first 3 hours after surgery.

Analysis of motor dysfunction: All sensorimotor testing was performed during the light cycle. Animals were pre-tested. A battery of sensorimotor tests was used. These tests are sensitive to damage produced by ICH and ischemia in this model and have been used successfully in the inventors' laboratory for two decades. Five functional outcomes (adhesive removal test, forelimb placing test, cylinder test, corner test and food fault test) were assessed in order to detect different embodiments of neurological outcome (motor, reflex, balance, and somatosensory) and provide greater confidence for consistent therapeutic benefits.

Brain Edema: The brain edema was measured using the wet-weight/dry-weight method. After perfused with PBS the brains were removed and frozen. The brain tissue was collected from three coronal brain sections (40 μm), representing levels of needle track (blood injection site) and 0.25 mm rostrally and caudally to the needle track. The tissue weight was determined before and after drying in an 80° C. oven overnight.

Hematoma size measurement: The hematoma resolution was assessed by measuring the amount of hemoglobin (Hb) remaining in the hematoma-affected brain at day 7 following ICH.

Power and Data Analysis: Initial power analysis is based on $\alpha=0.05$ and $\beta=0.2$ for all the experiments. A plan of n=10 was utilized for all the behavioral tests. n=5 for remaining tests. This should be sufficient to detect a difference of 20-25% based on the laboratory experience and the preliminary studies. Statistical analyses will be performed using Prism and InStat data analysis programs. A repeated two-way analysis of variance with Bonferroni post-hoc tests will be used to evaluate differences among groups and times. Remaining data will be analyzed using one-way analyses of variance (ANOVA). A Newman-Keuls post-hoc test will be used for multiple tests. The non-paired t test will also be used when only two groups are compared. Additional methodology details may be found in the following publications listed below 71, 79, 89, 92-94, 96, 97, 99-119.

Figure 8:
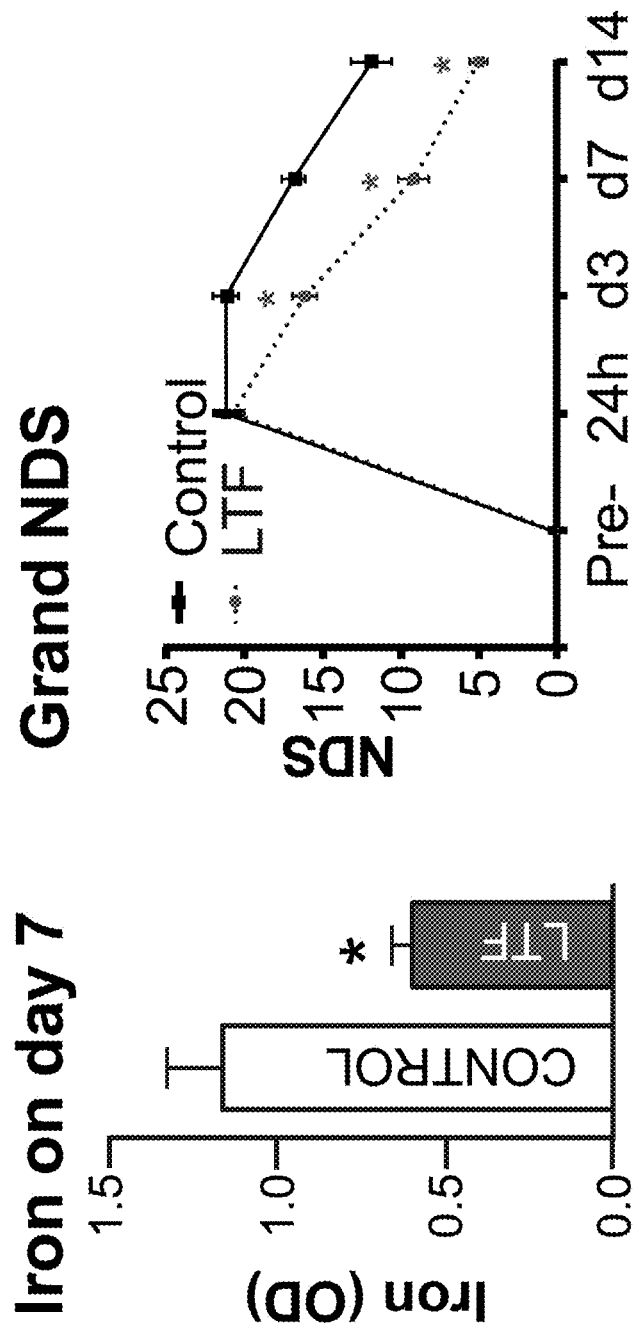
FIG. 8 shows (in the left panel) the remnant ferric iron (mean±SEM) in brain hematoma, measured with Prussian Blue reaction, on d7 after ICH. Right Panel: NDS (an index of neurological dysfunctions) at indicated times after ICH in Sprague Dawley rats treated with 10 mg/kg of rLTF at 24 h post ICH. *p≤0.05, between the two groups at indicated time points; n=9.

Treatment with LTF was determined to reduce symptoms of brain edema, iron deposition and neurological dysfunction after ICH in vivo, in rats. There is normally a negligible amount of LTF in a naïve rodent brain and there is a negligible level of LTF mRNA expression in the brain under normal conditions and following ICH. The results demonstrating a beneficial role of LTF in vitro, indicating that treatment with LTF has beneficial effects on ICH associated symptoms such as brain edema, iron deposition and neurological dysfunction in vivo. Indeed, rhLTF administered at a dose of 10 mg/kg, i.v., 30 min after ICH (using the clinically relevant autologous blood injection model of ICH), offered robust protection by reducing brain edema (brain water content of 76.4% vs. 78.1%; $p \le 0.05$; a 40.5% reduction vs. naïve control) as well as the neurological deficit (NDS) by 27.4% (14.3 vs. 19.7; $p \le 0.05$) on d3 after ICH. The NDS is a composite neurological deficit score from 5 individual well-validated behavioral tests: postural reflex, forward placing, foot fault, cylinder, and circling. Individual tests all demonstrated a significant improvement following treatment with rhLTF. In an additional study, treatment with rhLTF (10 mg/kg, i.v.) was delayed for 24 h after ICH onset. Even with this 24 h delay (see FIG. 8), the LTF remarkably reduced the NDS by 23.8% (on day 3), 45.7% (on day 7), and 57.8% (on day 14); and these functional benefits coincided with the improved clearance of hematoma (43.6%) and ICH-deposited iron (39.6%) on day 7 (see FIG. 8). In addition, the therapeutic dose of LTF reduced the formation of 4-hydroxynonenal (4-HNE; index of lipid peroxidation) by 47% in a ICH affected brain as measured at 3d after ICH, demonstrating therapeutic efficacy for LTF in reducing oxidative damage after ICH.

Example 4

Figure 9:
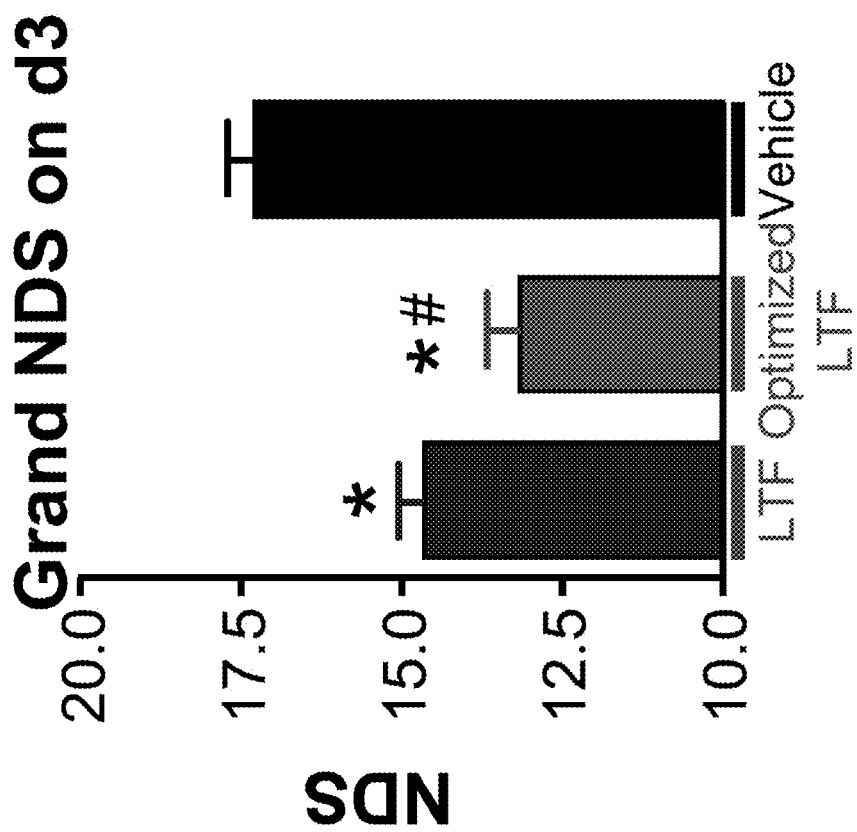
FIG. 9 depicts the Neurological Deficit Score (NDS) (an index of neurological dysfunction-aggregate score from placing, footfault and cylinder tests) at 3d after ICH in C57/BL mice subjected to ICH and treated with rLTF, optimized LTF (PRC14) or PBS at 24 h after the ICH onset. *p≤0.05 vs. vehicle, # p≤0.05 vs. LTF n=9.

Lactoferrin fusion protein is more effective than lactoferrin. Treatment with LTF-human IgG Fc-fusion protein (LTF-hIgG-Fc: PRC14) was determined to be more effective than LTF alone in reducing the symptoms and neurological dysfunction after ICH. To compare the therapeutic potential of LTF vs. LTF-human IgG2 Fc fusion protein (LTF-hIgG-Fc: PRC14): see FIG. 9), mice were subjected to ICH and 24 h later, and randomized them into 3 treatment groups. Group 1 received treatment with 10 mg/kg of rhLTF. Group 2: received treatment with 10 mg/kg LTF-fusion protein PRC14 (LTF-hIgG-Fc) see FIG. 9). Group 3 received saline vehicle only. All the treatments were delivered intravenously and the outcome was assessed behaviorally 2 days later (3 days after ICH). As compared with the vehicle control, treatment with both LTF and LTF-fusion protein PRC14 (LTF-hIgG-Fc) markedly reduced neurological deficit caused by ICH and associated symptoms, however, as judged using the result of assays such as placing, footfault or cylinder tests, individually or as composite score, the therapeutic effect of the LTF-fusion protein PRC14 (LTF-hIgG-Fc) was significantly stronger than that seen following treatment with LTF.

LTFs pleotropic modes of action appear to positively address the multifactorial pathobiology of ICH by among others (1) improving iron sequestration, (2) cytoprotection, (3) reducing pro-inflammatory responses, and (4) improving cleanup process (hematoma resorption/resolution). Also, the novel LTF-fusion protein PRC14 (LTF-hIgG-Fc) appears to be more effective than rhLTF. Indicating that LTF-human IgG Fc-fusion protein (LTF-hIgG-Fc: PRC14) is an effective ICH treatment.

Example 5

Treatment with different forms of LTF result in very gene expression patterns: Gene Expression Profile in Human Whole Blood Culture: Single blood bank donor venous blood (collected in EDTA Vacutainer) was diluted 1/5 in serum free RPMI 1640 (+L-glutamine and sodium bicarbonate, Cat# R8758: Sigma-Aldrich, St Louis, Mo., USA) supplemented with 2-Mercaptoethanol (5 mL/100 mL). Using a sterile container, a one cell suspension was prepared for distribution into 10 ml cell culture for different treatments.

Whole blood cell (WBC) cultures were established in sterile 50 ml conical tubes and the cells were treated for 2 hrs with rhLTF or PRC14 (LTF-hIgG-Fc) fusion protein in PBS, which was also used as the vehicle control. RNA was harvested from cultures containing cells treated with rhLTF and PRC14 (LTF-hIgG-Fc) fusion protein or an equal volume of PBS alone. RNA was subject to analysis using the Human Innate & Adaptive Immune Responses RT2 Profiler™ PCR Array (PAHS-052Z) which profiles the expression of 84 genes involved in the host immune response such as chemokines, cytokines and receptors.

The Human Innate & Adaptive Immune Responses $RT^2$ Profiler™ PCR Array profiles the expression of 84 genes involved in the host response to bacterial infection and sepsis. This array includes genes related to the IL-1R and Toll-like Receptor (TLR) Signaling Pathways including IL-1R and TLR genes involved in the detection of pathogens, as well as those associated with innate immunity and pattern recognition: receptors: DDX58 (RIG-I), NLRP3, NOD1 (CARD4), NOD2, TLR1, TLR2, TLR3, TLR4, TLR5, TLR6, TLR7, TLR8, TLR9; cytokines: CCL2 (MCP-1), CCL5 (RANTES), CSF2 (GM-CSF), CXCL10, IFNA1, IFNB1, IL18, IL1A, IL1B, IL2, IL8, TNF and other Genes: APCS, C3, CASP1 (ICE), CD14, CD4, CD40 (TNFRSF5), CD40LG (TNFSF5), CD8A, CRP, HLA-A, HLA-E, IL1R1, IRAK1, IRF3, IRF7, ITGAM, LY96 (MD-2), LYZ, MAPK1 (ERK2), MAPK8 (JNK1), MBL2, MPO, MX1, MYD88, NFKB1, NFKBIA (I/Ba/Mad3), STAT1, TICAM1 (TRIF), TRAF6. Those associated with adaptive immunity: Th1 markers/immune response: CCR5, CD80, CXCR3, IFNG, IL18, IL23A, SLC11A1, STAT4, TBX21, TLR4 and TLR6. Those associated with a Th2 markers/immune response: CCR4, CCR8, CD86, GATA3, IFNB1, IL10, IL13, IL18, IL4, IL5, IL6, NOD2, STATE; Those associated with Th17 Markers: CCR6, IL17A, RORC, STAT3; Those associated with Treg Markers: CCR4, CCR8, FOXP3 and IL10. Those associated with T Cell Activation: CD80, CD86, ICAM1, IFNG, IL23A, IL6 and SLC11A1; cytokines: CCL2 (MCP-1), CCL5 (RANTES), CSF2 (GM-CSF), CXCL10 (INP10), IFNA1, IFNG, IL10, IL13, IL17A, IL18, IL2, IL23A, IL4, IL5, IL6, IL8, TNF and other genes: CD4, CD40 (TNFRSF5), CD40LG (TNFSF5), CD8A, CRP, FASLG (TNFSF6), HLA-A, IFNAR1, IFNGR1, IL1B, UM, IRF3, IRF7, ITGAM, JAK2, MAPK8 (JNK1), MBL2, MX1, NFKB1, RAG1 and STAT1. Those associated with humoral immunity: C3, CCL2 (MCP-1), CCR6, CRP, IFNB1, IFNG, IL6, MBL2, NOD2 and TNF. Those associated with the inflammatory response: APCS, C3, CCL5 (RANTES), CRP, FOXP3, IL1A, IL1B, IL4, IL6, MBL2, STAT3 and TNF. Those associated with defense response bacteria: IFNB1, IFNG, IL23A, IL6, LYZ, MBL2, MYD88, NOD1 (CARD4), NOD2, SLC11A1, TLR1, TLR3, TLR4, TLR6, TLR9 and TNF. Those associated with the response elicited by viruses: CD4, CD40 (TNFRSF5), CD86, CD8A, CXCL10 (INP10), DDX58 (RIG-I), HLA-A, IFNAR1, IFNB1, IL23A, IL6, IRF3, NLRP3, TICAM1 (TRIF), TLR3, TLR7, TLR8 and TYK2.

Figure 10:
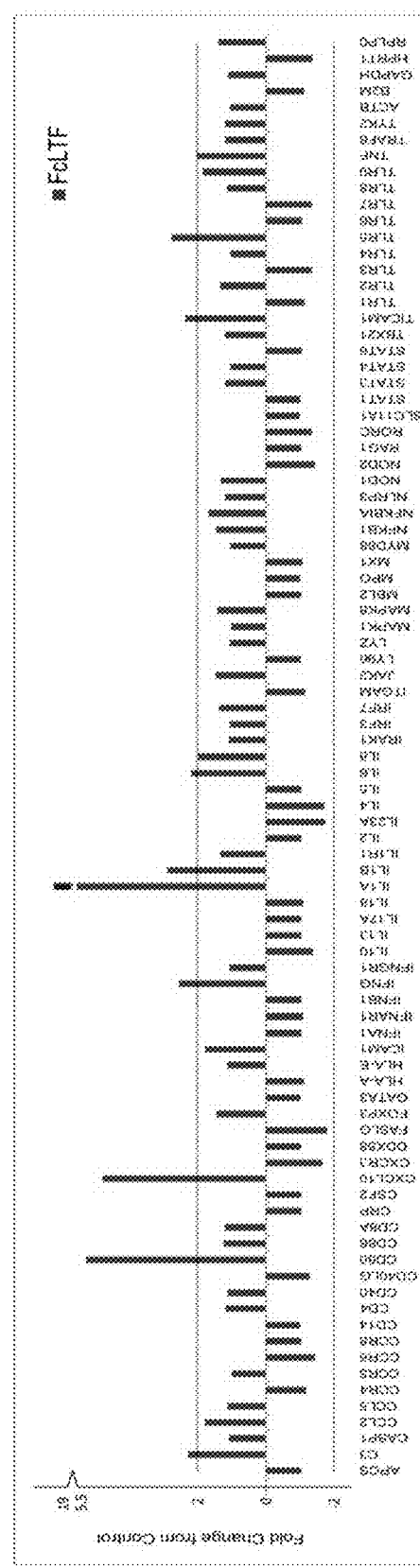
FIG. 10 the activation of genes in Network 1 by lactoferrin fusion protein (FcLTF).
Figure 11:
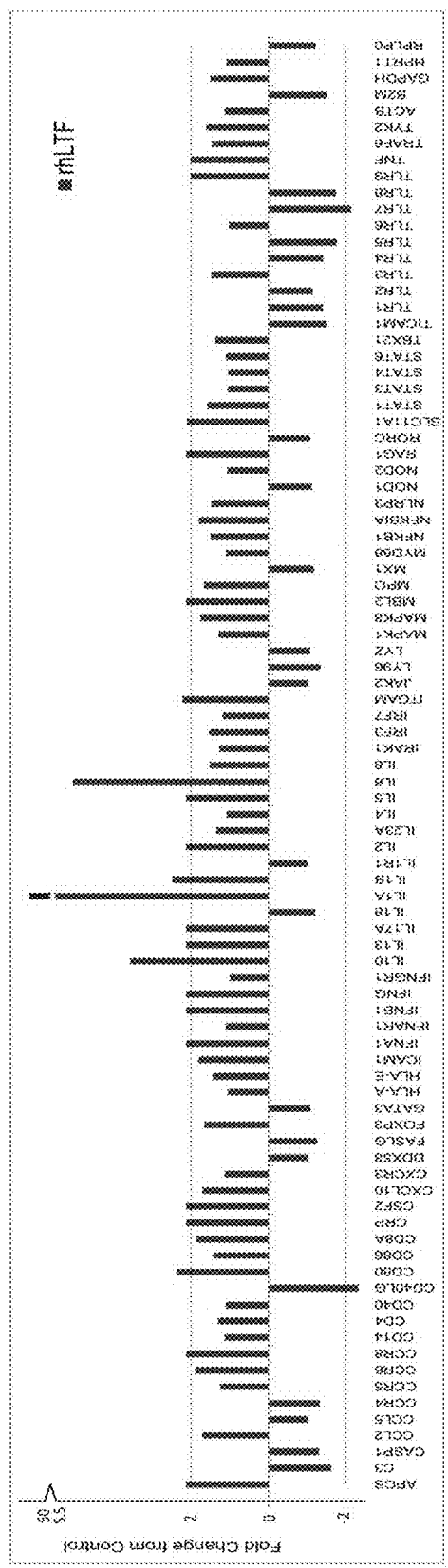
FIG. 11 the activation of the genes in Network 1 by rhLTF shows that exposure of WBCs to FcLTF results in a much higher level of expression of IL1A (>50 fold increase) and to expression of IL17a dimer, while exposure of WBCs to rhLTF inhibited (<20 fold) the expression of the same IL17a dimer.

Studies indicated that the gene expression profile of human WBC varied depending on the form of lactoferrrin, specifically treatment with LTF-fusion protein PRC14 (LTF-hIgG-Fc) or LTF can have very different effects on genes expressed, as indicated by the result obtained when WBC were exposed to LTF-fusion protein PRC14 (LTF-hIgG-Fc): FIG. 10) or to Lactoferrin (LTF: FIG. 11).

Figure 12:
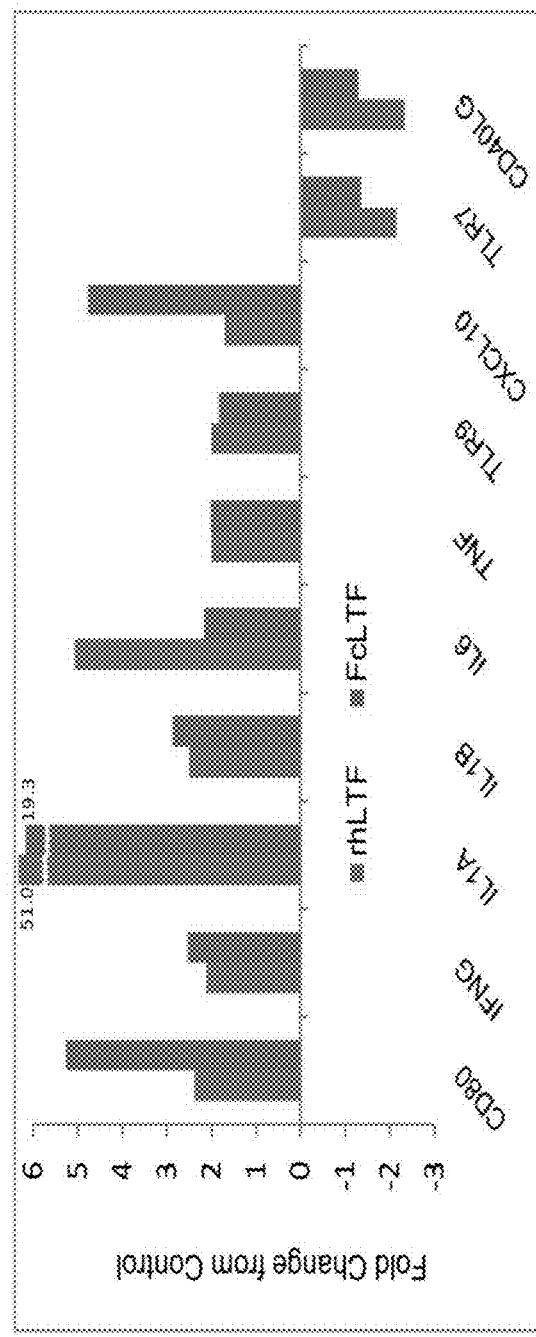
FIG. 12 Illustrates that exposure of whole blood cells to rhLTF increases the expression of IL6 which in turn leads to activation of chemokines. However, exposure of WBCs to FcLTF results in a lower level of expression of IL6 and thus a lower level of the expression of chemokines.

FIG. 12 illustrates that CD80, IFNG, IL1A, IL1B, IL6, TNF, TLR9, CXCL10, TLR7 and CD40LG gene expression patterns were similar, but differed with regard to degree of expression when human cells were exposed to LTF-fusion protein PRC14 or rhLTF.

Figure 13:
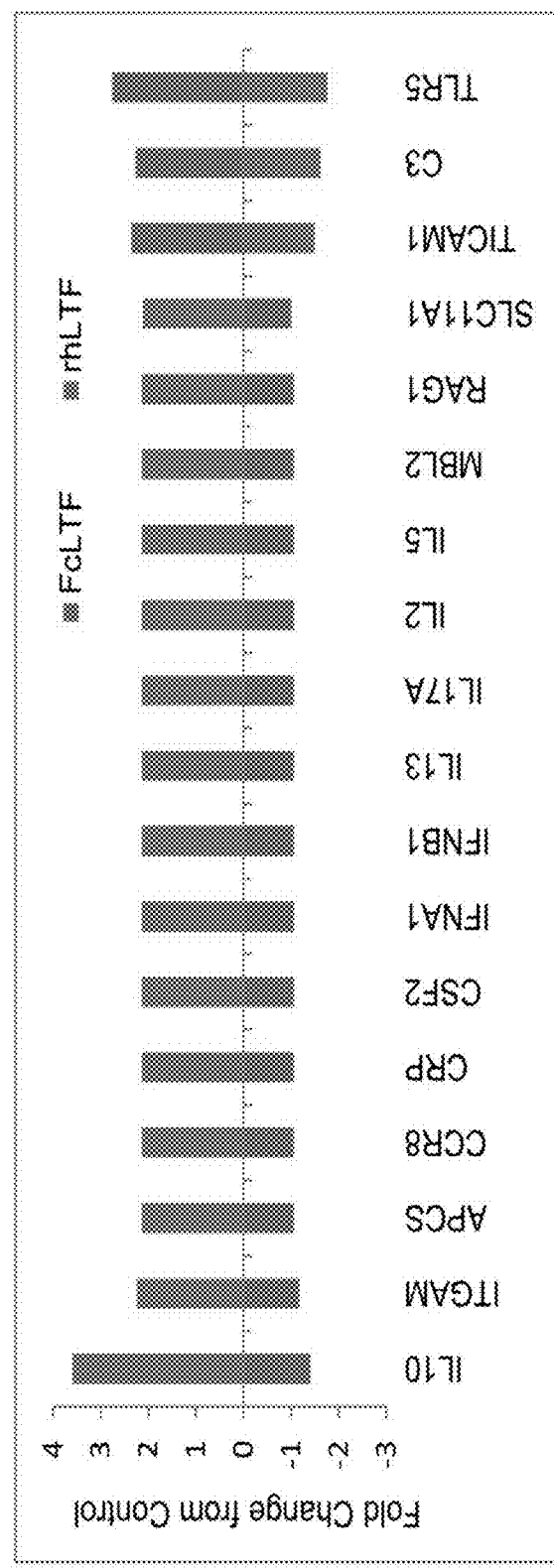
FIG. 13 Illustrates that exposure of WBCs to rhLTF increases the expression of IL10 (>3 fold) which leads to the activation of expression of MHC Class 1, TH1 cytokine, INFA1/IFNA13 and IL17. While, exposure of WBCs to FcLTF decreases expression of IL-10 (−1.5 fold) and appears to reduce the expression of the same genes (MHC Class 1, TH1 cytokine, INFA1/IFNA13 and IL17).

FIG. 13 illustrates the genes for which expression patterns were opposite in their pattern of expression when WBC were exposed to LTF-fusion protein PRC14 or rhLTF.

To determine if these patterns of gene expression were indicative of the activation or suppression of a particular metabolic pathway, these expression patterns were grouped into Networks, as shown in FIG. 14.

Activation of the genes in Network 1, by either LTF-fusion protein PRC14 or rhLTF showed that exposure of human cells to LTF-fusion protein PRC14 did not stimulate as great an increase (<20 fold) in the expression of the IL17a dimer or the IL-1R genes, as did exposure of human cells to rhLTF which resulted in a much higher level of expression of ILIA (>50 fold increase) and of IL17a dimer.

Activation of the genes in Network 2 by either LTF-fusion protein PRC14 or rhLTF showed that exposure of human cells to LTF-fusion protein PRC14 resulted in a lower level of expression of IL6 and thus a lower level of the expression of chemokines and caspase, than did exposure of WBCs to rhLTF, which resulted in increases in the expression of IL6 and activation of chemokines as well as caspase.

A very different pattern of gene expression resulted of exposure to LTF-fusion protein PRC14. LTF-fusion protein PRC14 exposure decreased expression of IL-10 (−1.5 fold) and appears to have reduced the expression of the same genes (MHC Class 1, TH1 cytokine, INFA1/IFNA13 and IL17) that are increased by exposure to rhLTF, which increased the expression of IL10 (>3 fold) and activation of expression of MHC Class 1, TH1 cytokine, INFA1/IFNA13 and IL17.

Another very different gene expression pattern resulted from exposure to LTF-fusion protein PRC14 and rhLTF but this time in Network 1 genes. Exposure of human cell cultures to rhLTF increased expression of IL13 and results in decreased expression of TLR5 and decreased expression of Janus kinase (JAK) expression. In contrast exposure to LTF-fusion protein PRC14 decreased expression of IL13 and activated expression of TLR5 and JAK.

Example 6

Pharmacokinetics of lactoferrin versus lactoferrin fusion protein (PRC14). In a study to determine the comparative pharmacokinetics of CHO-expressed rhLTF and the LTF-fusion protein PRC14 when administered as a single intravenous injection to Wistar rats. All procedures in this protocol were in compliance with the Animal Welfare Act, the Guide for the Care and Use of Laboratory Animals, and the Office of Laboratory Animal Welfare.

Test System: 230-250 gram Wistar Rats, both males and females, were obtained from Harlan Laboratories, (Indianapolis, Ind., USA). Upon receipt at the vivarium, rats were examined by trained personnel to ensure acceptable health status.

Rats were housed 1 per cage. Cage size met or exceeded the requirements set forth by the ILAR Guide for the Care and Use of Laboratory Animals. The rats were kept in a room maintained at 64 to 84° F. (22-24° C.) with humidity set at 40 to 70%. The room was illuminated with fluorescent lights timed to give a 12-hour light, 12-hour dark cycle. Standard rodent diet (Purina LabDiet 5001) and water were available ad libitum for all rats. The feed was analyzed by the supplier detailing nutritional information and levels of specified contaminants.

Test Materials: The test materials were provided by PharmaReview Corp. CHO-expressed recombinant human lactoferrin (rhLTF) was provided in a glass vial containing 5 mg of test material. LTF-fusion protein PRC14 was supplied in plastic vials, each containing 0.5 mg of lyophilized protein. Test articles were formulated as specified by formulation instructions, provided by PharmaReview Corp. The lyophilized preparations were reconstituted for administration with water for Cell Culture Applications, Cat #17-724Q (Lonza Group Ltd., Basel, Switzerland).

Preparation of stock solution of rhLTF: Five mg of rhLTF was dissolved in 5 ml of deionized sterile water (and aliquoted if desired) before freezing for longer storage periods (weeks/months). It was active when stored at 4 degrees C. for a week or two.

Preparation of stock solution of LTF-fusion protein PRC14: In order to account for the difference in the molecular structure of LTF-fusion protein PRC14 and that of rhLTF, the concentration of LTF-fusion protein PRC14 was normalized for LF equivalency at 1 mg/ml.

Storage Conditions: All test materials were stored at 4° C. until formulated. Formulated material was stored at ambient laboratory temperature during dosing. Approximately 100 µL of each formulated test article was frozen with samples for ELISA testing.

Test Article Administration: Each animal was weighed and catheters tested for patency and pre-dose blood samples were obtained. Dose volumes were calculated based on individual body weights and an injection volume of 1 mL/kg was used. Animals were restrained in Broome-style restrainers for dosing, during which tails were warmed by immersing in ~40° C. water bath for approximately 10 seconds. Tails were swabbed with an alcohol soaked gauze pad, and a bolus intravenous dose was delivered into the lateral tail vein of each animal.

Sampling: At the selected collection timepoints (pre-dose, 1, 5, 10, 20, 40, 80, 160, and 320 minutes) blood was collected through a jugular vein catheter that had been inserted into each rat. Following the removal of the pin from the catheter, approximately 100 µL of material was aspirated from the catheter and disposed of and then the following approximately 250 µL of blood was collected for testing. Catheters were then flushed with 200 µL of saline following each blood collection. The blood sample was placed in $K_2EDTA$ tube and inverted 10 times before being placed on ice, until centrifugation at 8000 rpm for 5 minutes at 4° C. Plasma was decanted into labeled Eppendorf tubes and frozen at −80° C. until ELISA testing.

ELISA testing: Plasma samples were assayed for lactoferrin concentrations using AssayPro Human Lactoferrin ELISA Kit (Catalog# EL2011-1: ASSAYPRO LLP, St. Charles, Mo., USA), as per the manufactures protocol, with the exception of sample dilutions used. Plasma samples were diluted 1:1200 (one part plasma to 1,199 parts sample buffer) and Test Articles 1:500,000 (one part test article to 499,999 parts sample buffer).

Figure 15:
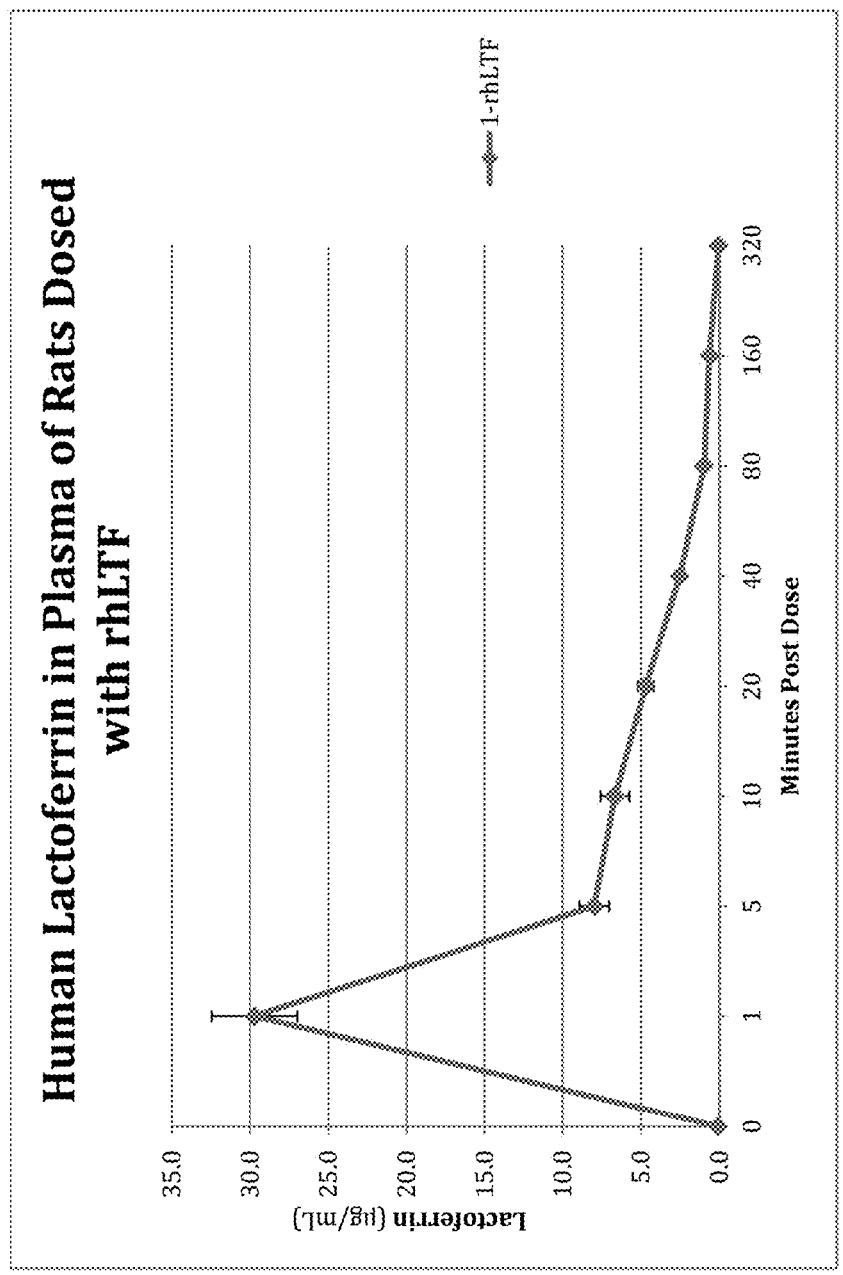
FIG. 15 shows pharmacokinetic data for recombinant human lactoferrin (rhLTF) calculated using WinNonlin and based on the mean values per group, per timepoint. Data points were corrected by subtracting value for 0 minute timepoint from all timepoints
Figure 16:
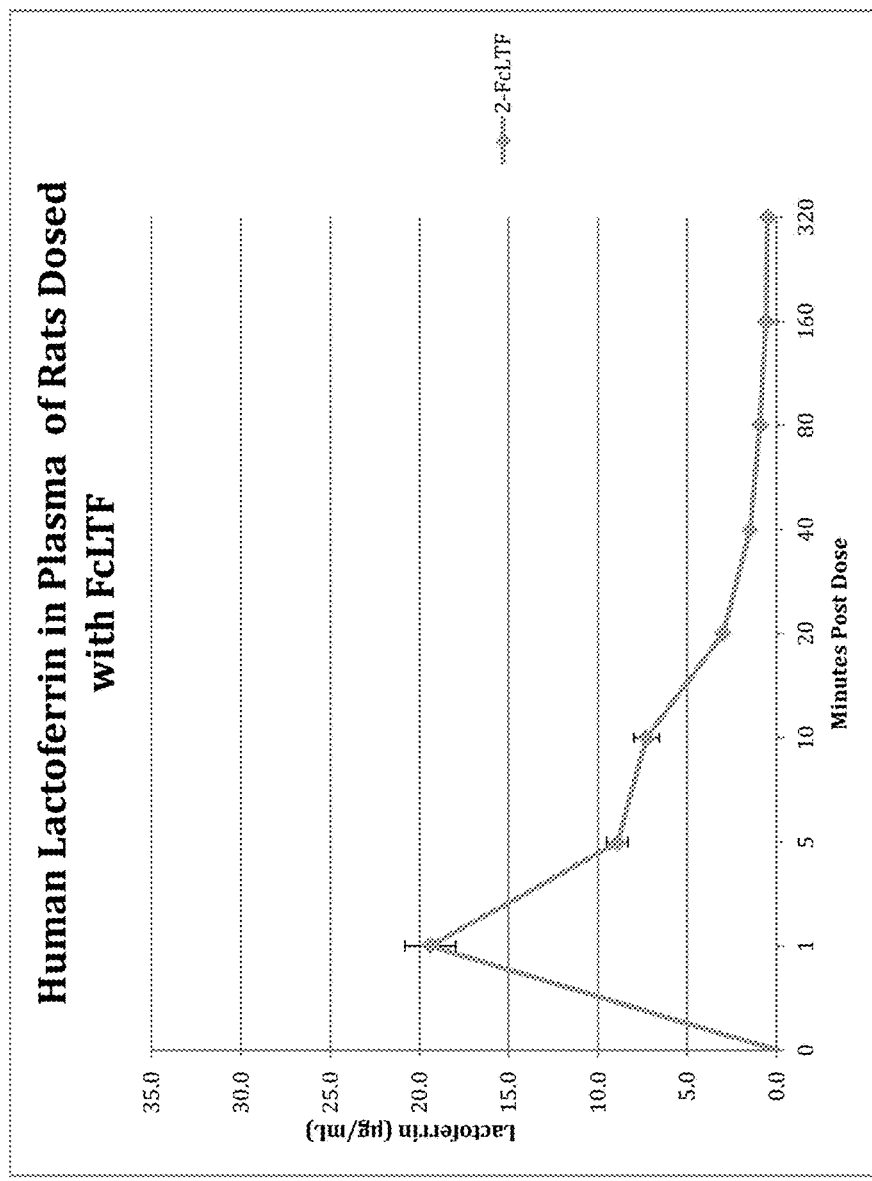
FIG. 16 shows pharmacokinetic data for recombinant lactoferrin fusion protein (FcLTF: PRC 14) calculated using WinNonlin and based on the mean values per group, per time point. Data points were corrected by subtracting value for 0 minute time point from all time points

Pharmacokinetic Results: Pharmacokinetic Data was calculated using WinNonlin and based on the mean values per group, per timepoint. Data points were corrected by subtracting value for 0 minute timepoint from all timepoints and are presented in FIG. 15 and FIG. 16.

Table 1 illustrates the rise in LTF levels that occurred between the 0 to 320 minute time points for animals treated with rhLTF or LTF-fusion protein PRC14. The table presents Half-Life, Area Under the Curve (AUC), maximal Concentration (Cmax), Mean Retention Time (MRT), Volume distribution (Vd) and Clearence (CL). The Half-Life and Mean Retention Time (MRT) were significantly increased for the LTF-fusion protein PRC14 as compared to LTF alone.

TABLE 1

| Treatment Group | Half-Life (min) | AUC∞ (µg-min/mL) | Cmax (µg/mL) | MRT (min) | $V_d$ (mL) | CL (mL/min/kg) |
|---|---|---|---|---|---|---|
| rhLTF | 39.68 | 407.98 | 29.64 | 44.35 | 143.48 | 2.51 |
| Fc2LTF | 231.00 | 629.19 | 19.47 | 253.94 | 550.91 | 1.65 |

Example 7

Figure 17:
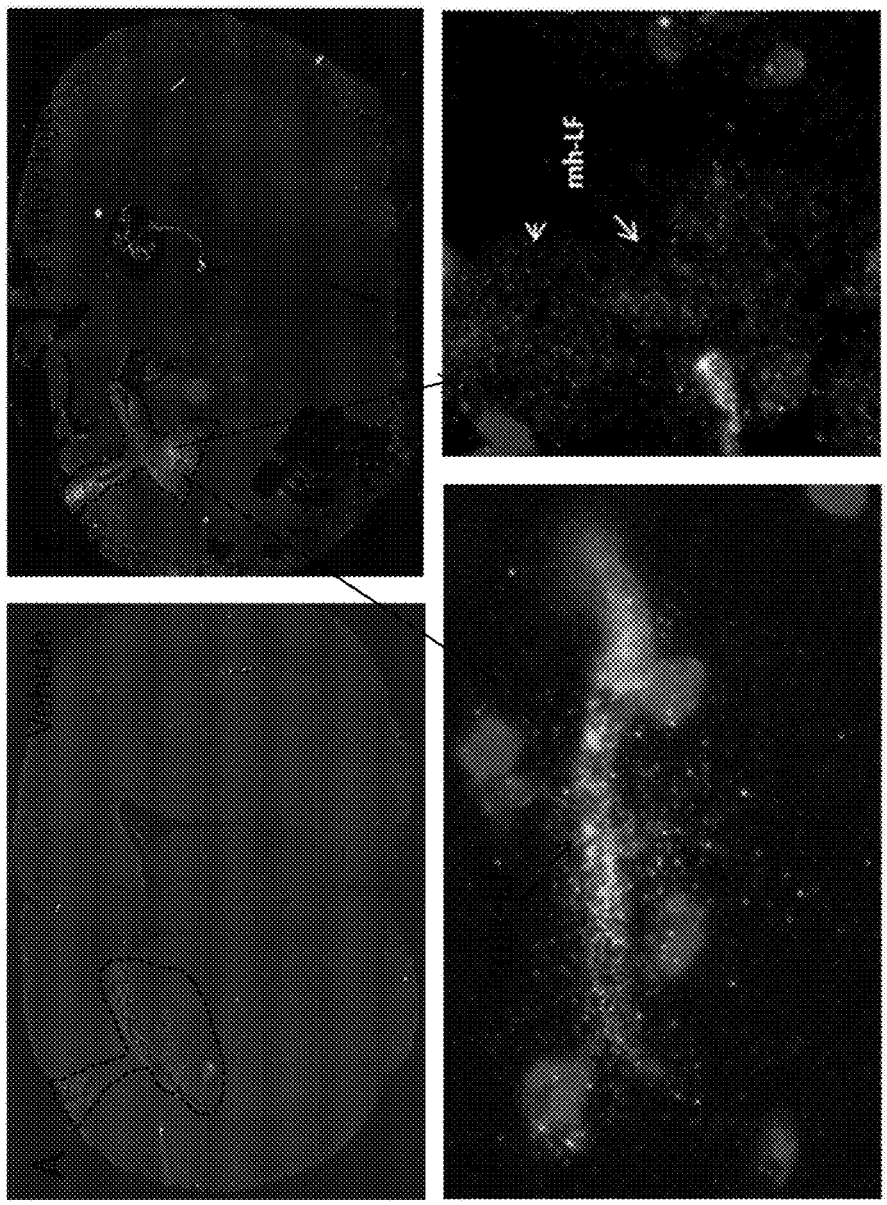
FIG. 17 shows lactoferrin immunofluorescence in the mouse brain. 6 h after ICH animals received treatments with intravenous saline (panel A) or 50 mg/kg of PRC14 (panel B), and 3 h later brains were analyzed for the presence of lactoferrin using immunohistochemistry. Green indicates tissue that contains lactoferrin. The read outlined field highlights the ICH-affected brain at a coronal brain section. Note that brain from animals that were injected with PRC14 (panel B) contain large amounts of lactoferrin. This indicates that PRC14 entered ICH affected brain. Panels C and D are high magnifications of the brain in panel B, showing abundance of PRC14 in the brain of treated animals. Note that the lactoferrin at the ICH-affected brain area is present around the blood vessels (labeled CD31; red).

In vivo evidence of effective therapy. Six hours after ICH animals received either intravenous injections of saline (FIG. 17A) or 50 mg/kg of optimized lactoferrin fusion protein (PRC14: FIG. 17B) and 3 hours after therapy, the animals were sacrificed and the brains harvested for analysis of the presence of lactoferrin using immunohistochemical techniques. Green fluorescence indicates tissue that contains human lactoferrin (indicative of presence PRC14; this anti-human lactoferrin antibody do not recognize mice lactoferrin) and the dashes encompass an area of ICH-affected brain, on a coronal brain section. It may be seen that the brain sections from animals that were injected with optimized lactoferrin fusion protein (PRC14) contain large amount of lactoferrin, as shown in FIG. 17B. Under higher magnification, the highlighted area of FIG. 17 B, illustrates an abundance of lactoferrin in the brains parenchyma (outside of vessel) of animals treated with optimized lactoferrin fusion protein (PRC14). These results indicate that brain from animals that were injected with optimized lactoferrin fusion protein (PRC14) contain large amount of lactoferrin. FIG. 17C and FIG. 17D are higher magnification images of the region of interest in the brain sections shown in FIG. 17B. One can see an abundance of green fluorescence (lactoferrin) in the brain of animals treated with optimized lactoferrin fusion protein (PRC14). As expected, it appeared that these lactoferrin depositions occurred in the region of blood vessels (identified using labeled CD31). These findings indicate that i.v. injected optimized lactoferrin fusion protein (PRC14) enters ICH affected brain and deposits lactoferrin.

A study was designed to compare the effect of treatment with lactoferrin (recombinant human lactoferrin: rhLTF) to treatment with optimized lactoferrin fusion protein (PRC14) on mice with ICH. To evaluate the efficacy of treatments for ICH, a series of tests that combined generate a composite Neurological Deficit Score (NDS), known as Grand NDS, was determined using a set of behavioral tests such as postural flexing, forward placing, foot faults and cylinder. Mice (9 per group) were assigned to each group and evaluated prior to treatment and on day 1 (d1; black) and day 3 (d3; blue) after therapy. Therapy consisted of bolus intravenous injections of either 10 mg/kg of lactoferrin (rhLTF), 10 mg/kg of optimized lactoferrin fusion protein (PRC14) or vehicle (saline), followed by oral doses on d2 and d3 of 1 mg/kg.

Figure 18:
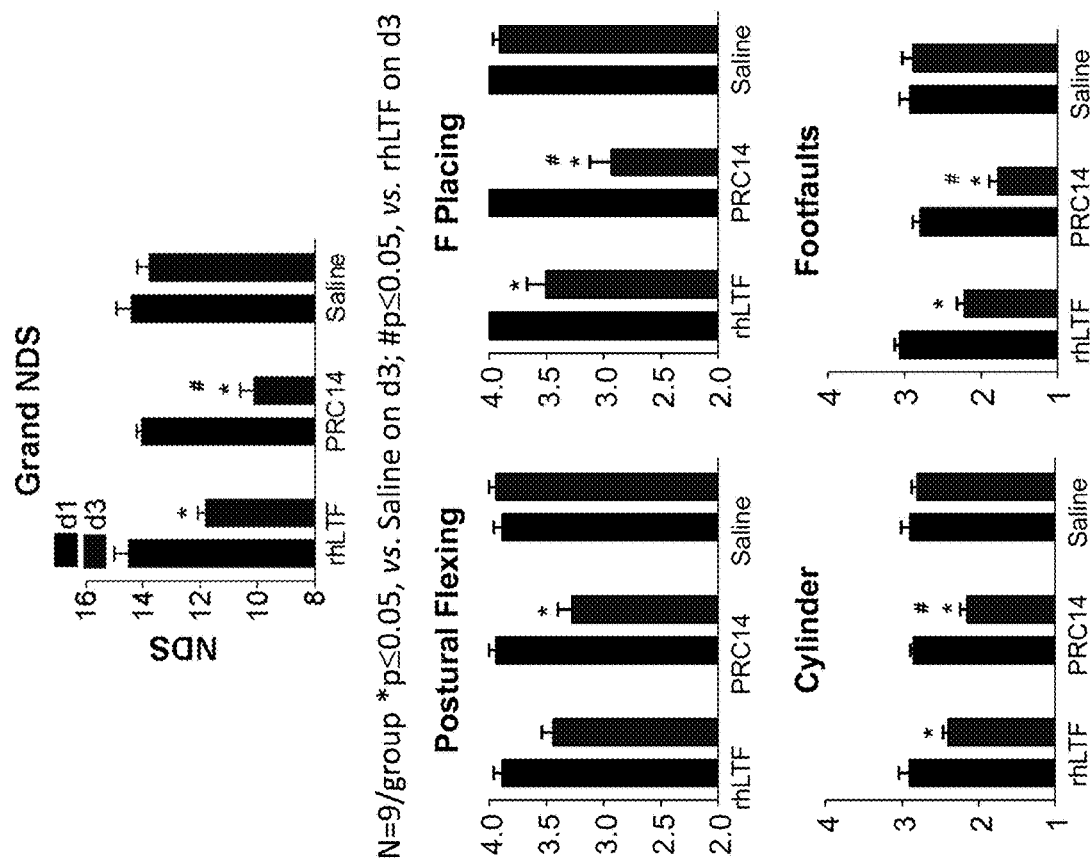
FIG. 18 shows the effects of rhLTF and PRC14 (optimized LTF) on Neurological Deficit Score (NDS) in mice following ICH. Grand NDS (A composite score showing neurological deficit scores measured by using a set of behavioral tests: Postural flexing, Forward Placing, Footfaults and Cylinder) was evaluated before treatment (d1; black) and 3 days (d3; blue) after treatments with bolus iv injection of 10 mg/kg of rhLTF, PRC14 or vehicle (saline) and followed by oral at d2 and d3 at 1 mg/kg. *$p \leq 0.05$, compared with the vehicle control group at the same time point (d3 after ICH). # $p \leq 0.05$, compared with the rhLTF group on d3. The effect of treatment with PRC14 reduce NDS is superior to rhLTF.

FIG. 18 illustrates that while both treatment with lactoferrin or optimized lactoferrin fusion protein significantly reduced the symptoms observed on d1 (*p>0.05, as compared to the vehicle control group at the same time point after ICH) by d3, the optimized lactoferrin fusion protein (PRC14) therapy was more effective than lactoferrin (rhLTF).

Figure 19:
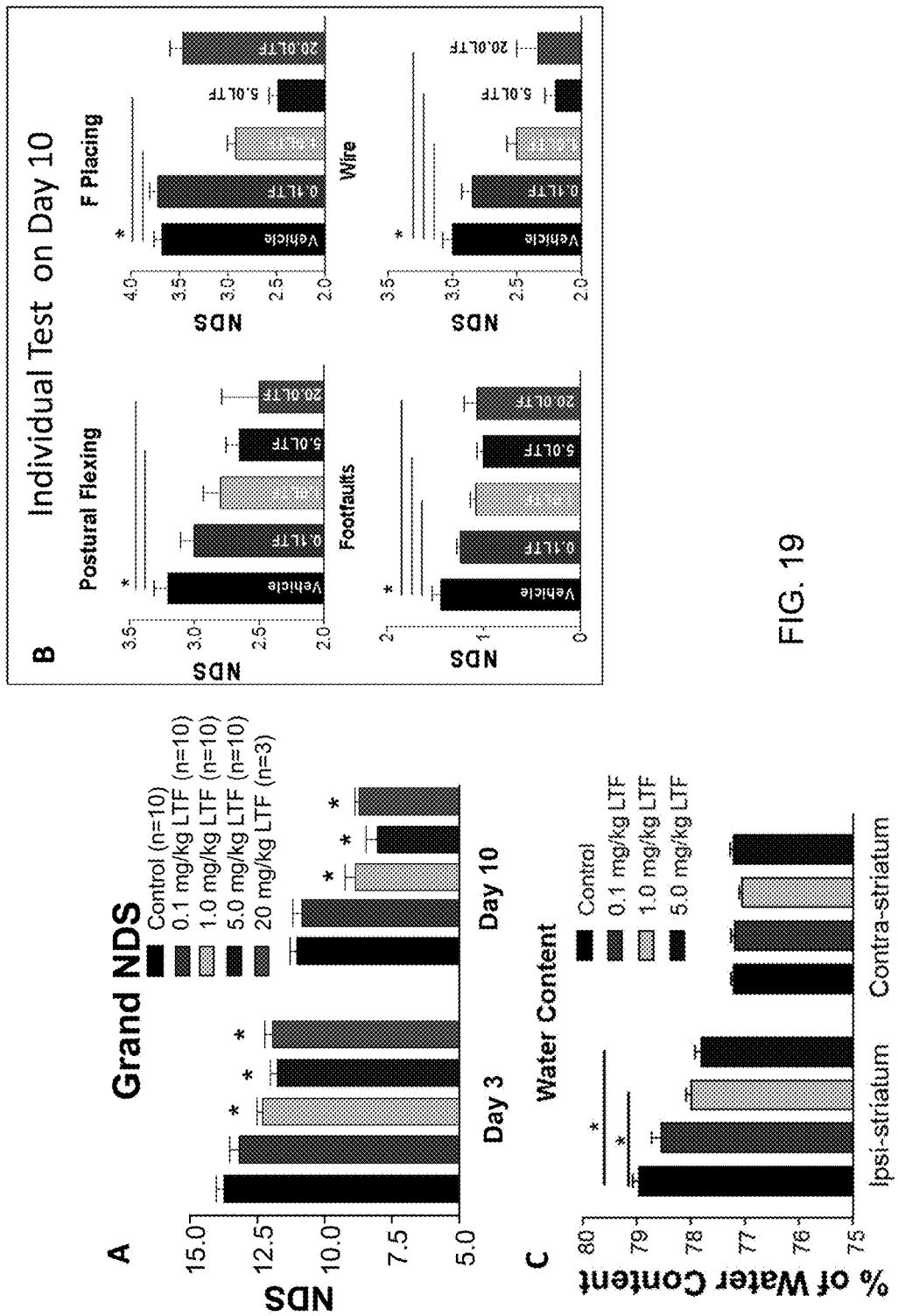
FIG. 19 shows the dose response of PRC14 on neurological deficit (NDS) and brain edema in mice after ICH. Panel A: Grand NDS (composite of individual tests) on d3 and d10, Panel B: Score for performance at each individual behavior test (Postural Flexing, Forward Placing, Footfaults and Wire) on d10 after ICH, and Panel C: brain edema on d3 (brain water content in the ICH-affected striatum (Ipsi) and the contralateral striatum (Contra), mean±SEM, n=5). The PRC14 (0.1-20 mg/kg) was administered first at 3 h after ICH by i.v. infusion and then by i.p. injection on d1 and d2. *$p \leq 0.05$, compared with the indicated group. Although in all three groups PRC14 at 1, 5 and 20 mg/kg were effective, the 5 mg/kg group appears to provide the optimal protection of the neurological functional recovery and brain edema.

To determine the desired dosage, a dose response study was performed for optimized lactoferrin fusion protein (PRC14) therapy on the neurological deficit score (NDS: shown in FIG. 19 panel A) Score for performance at each individual behavior test (Postural Flexing, Forward Placing, Footfaults and Wire, shown in FIG. 19 Panel B) and brain edema (shown in FIG. 19 panel C) in mice with ICH.

The optimized lactoferrin fusion protein (PRC14) therapy was administered first at 3 h after ICH (clinically relevant delay) by intravenous infusion and then by intraperitoneal (i.p.) injection on day 1 and day 2. Dosages ranged from 0 mg/kg, 0.1 mg/kg, 1 mg/kg, 5 mg/kg and 20 mg/kg were administered to groups of animals (n=10, n=10, n=10, n=10 and n=3, respectively). The results shown in FIG. 19, panel A are presented and characterize the effect of various treatment dosages on Grand NDS (composite of individual tests) results obtained on day 3 and day 10 after ICH. The results shown in FIG. 19, panel B are presented as to effect of various treatment dosages on score for performance in each individual behavior test (Postural Flexing, Forward Placing, Footfaults and Wire) on d10 after ICH. The results shown in FIG. 19, panel C are presented as to effect of various treatment dosages on brain edema on day 3 (brain water content in the ICH-affected striatum (Ipsi) and the contralateral striatum (Contra) after ICH (data are presented as mean+/−SEM (n=5), *P>0.05, compared with the indicated group).

Although treatment with three dosages of 1, 5 and 20 mg/kg, of optimized lactoferrin fusion protein (PRC14) had an effect of reducing ICH symptoms significantly, treatment with 5 mg/kg appeared to provide an optimal protection on both functional neurological recovery and brain edema.

Figure 20:
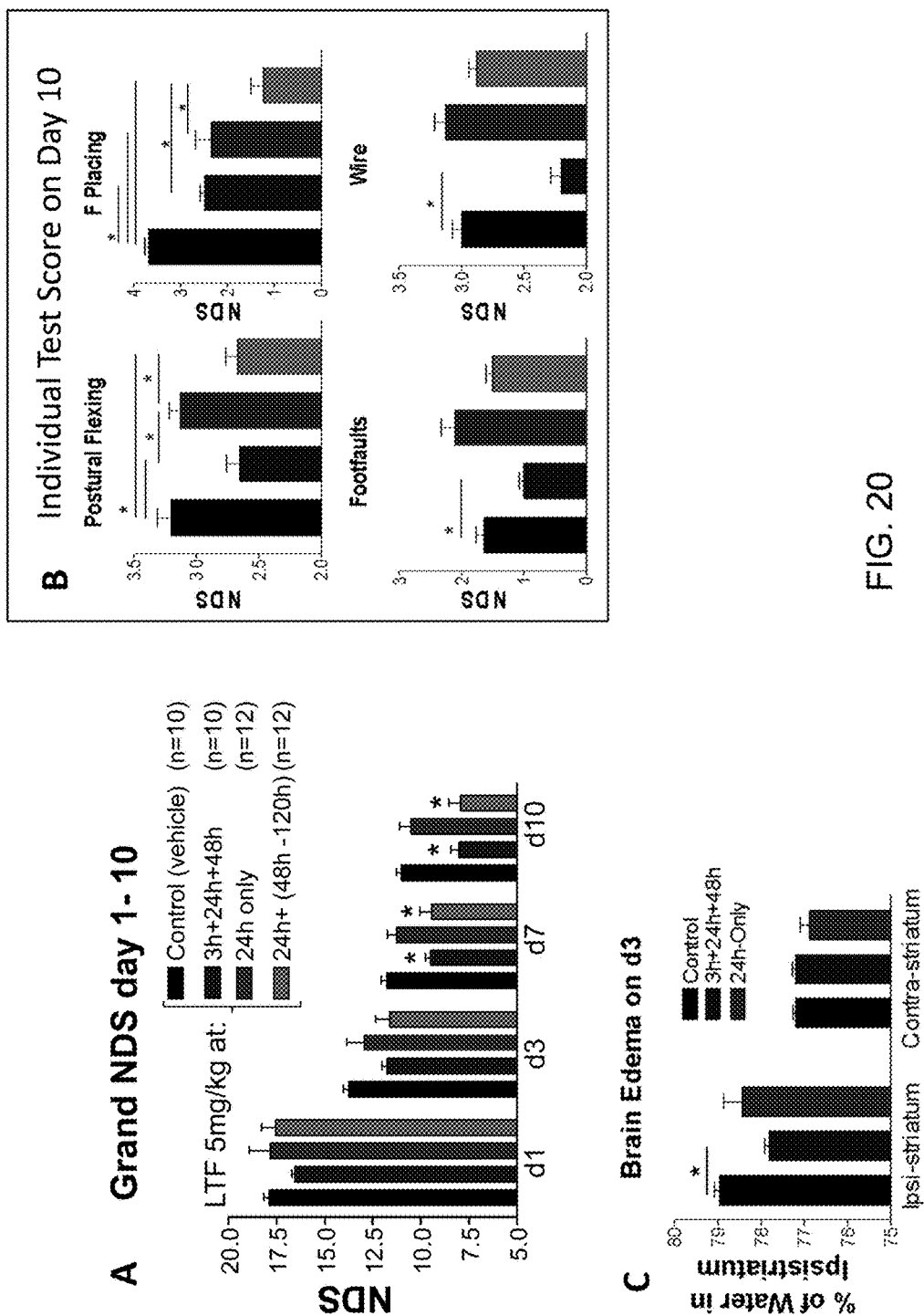
FIG. 20 shows the effects of PRC14 (at 5 mg/kg) given as indicated in figure legend for Panel A on reduction of NDS (Panels A & B) and brain edema (Panel C) in mice after ICH. Panel A: Effect on Grand NDS on d1, d3, d7 and d10. Panel B: Effect on individual behavior test score (Postural Flexing, Forward Placing, Footfaults and Wire) on d10 after ICH. Panel C: Effect on brain edema on d3 (brain water content in the ICH-affected ipsilateral (Ipsi) striatum and the contralateral (Contra) striatum, mean±SEM, n=5). PRC14 (5 mg/kg) was administered 1) 3 h+24 h+48 h; 24 h only; or (24 h+d2, d3, d4, d5). *$p \leq 0.05$, compared with the vehicle control group at the same time point.

To determine a desired therapeutic dosing regimen, a study was performed for o optimized lactoferrin fusion protein (PRC14) therapy on the neurological deficit score (NDS: shown in FIG. 20 panel A) Score for performance at each individual behavior test (Postural Flexing, Forward Placing, Footfaults and Wire, shown in FIG. 20 panel B) and brain edema (shown in FIG. 20 panel C) in mice with ICH.

The optimized lactoferrin fusion protein (PRC14) therapy was administered, at a dosage of 5 mg/kg, to four groups of mice with ICH. One group (n=10 mice) received saline only (untreated control group); a second group (n=10 mice) received treatment with optimized lactoferrin fusion protein (PRC14) at 3 hours, 24 hours and 48 hours; a third group (n=12 mice) received treatment with optimized lactoferrin fusion protein (PRC14) at 24 hours only; and a forth group (n=12 mice) received treatment with optimized lactoferrin fusion protein (PRC14) at 24 hours (day 1); day 2, day 3, day 4 and day 5.

The results shown in FIG. 20, panel A are presented as to effect of the timing of various treatment regimens on Grand NDS (composite of individual tests). The results shown in FIG. 20, panel B are presented as to effect of the timing of various treatment regimens on the score for performance in each individual behavior test (Postural Flexing, Forward Placing, Footfaults and Wire) as determined on d10 after ICH. The results shown in FIG. 20, panel C are presented as to effect of the timing of various treatment regimens on brain edema on day 3 (brain water content in the ICH-affected striatum (Ipsi) and the contralateral striatum (Contra) after ICH (data are presented as mean+/−SEM (n=5), *P>0.05, compared with the indicated group).

The results of this study show that mice with ICH, treated with optimized lactoferrin fusion protein (PRC14) administered at a dosage of 5 mg/kg in a dosing regimen of 3 hours, 24 hours and 48 hours received the best effect and significant reductions in symptoms associated with ICH, specifically a reduction in the symptoms of Grand ND Scores, performance in each individual behavior test (Postural Flexing, Forward Placing, Footfaults and Wire) at day 10, and in the levels of brain edema in mice after ICH.

Example 8

PRC14 demonstrates therapeutic effect in large animal (pig) model of intracerebral hemorrhage (ICH).

Earlier studies with the rodents identified PRC14 as effective therapy for ICH, regarding reduction in neurological definite, edema and improved (faster) hematoma clearance with at least 24 h therapeutic window of opportunity. Since one of the limitations of the rodent ICH model is small hematoma size, a piglet model of ICH (which not only offers gyrencephalic brain with abundant presence of white matter (similar as in humans), but also due to a larger volume of hematoma, longer lasting presence of blood in the brain) was utilized. In rodent hematoma is fully cleared within less than 2 weeks.

Induction of ICH and MRI. Male Yorkshire pigs with average age/weight of 8 wk/13.4±2.4 kg were used. Pigs were sedated with ketamine (25 mg/kg, IM) and maintained under isoflurane during the surgery. During this surgery, animals were intubated and the right jugular artery was catheterized for monitoring blood pressure, blood gases, and glucose concentrations. Body temperature was maintained at 37.5° C. by blanket. A cranial burr hole (1.5 mm diameter) was drilled 11 mm to the right of the sagittal and 11 mm anterior to the coronal suture. An 18-mm 20-gauge sterile plastic catheter was placed stereotaxically into the center of the right frontal cerebral white matter (centrum semiovale) at the level of the caudate nucleus and cemented in place. Lobar ICH was induced by pressure controlled infusion of 1.0 mL of autologous blood into the right frontal hemisphere over 10 minutes. After a 5-min break, another 1.5 ml of blood was injected over 6 minutes. Despite of standardize amount of blood injected each time the volume of resulting hematoma varies in size (likely due to leakage of blood to ventricles or subarachnoid space) and at 24 h after ICH onset average was 1.08+/−0.77 ml (Mean+/−SD; n=12), ranging from 2.2 ml to 0.3 ml among animals.

Figure 21:
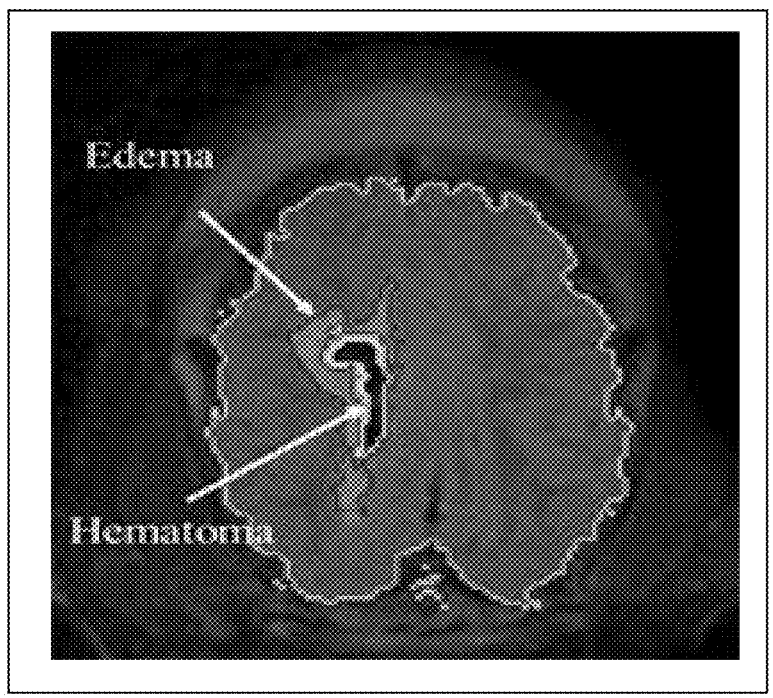
FIG. 21 Shows a follow-up scan of a pig brain imaged on day 7 following surgery to induce ICH demonstrating hematoma and edema.

The pigs were imaged one day after the surgery with a follow-up scan on day 7. During scanning, animals were ventilated with average 18 breath-per-minute with maximum airway pressure of 20 cm-H2O, oxygen saturation level (SpO2) of 97%, typical end tidal CO2 of 47 mmHg, heart rate 120 beat-per-minute, and body temperature 98.6° C. Anesthesia was maintained with 2% isoflurane mixed with oxygen. Animals were positioned prone in 3.0 Tesla Philips Ingenia MRI system (Philips, Best, Netherland) and imaged using 15-channel head coil. Anatomical imaging included: 3D fluid attenuated inversion recovery (FLAIR, TR/TE=4800/383 ms, FOV=200×200×64 mm3). A semi-automated seed-growing algorithm using Analyze 10.0 (Analyze Direct Inc., KS, USA) was used to delineate hematoma and edema volume on FLAIR images (FIG. 21).

Treatment paradigm. PRC14 dissolved in 200 ml of saline was delivered intravenously as a drip over 15-20 min. Each animal received either PRC14 or saline (control) six times. First treatment was delivered 6 h after the onset of ICH and then continued once a day until day 6.

Figure 22:
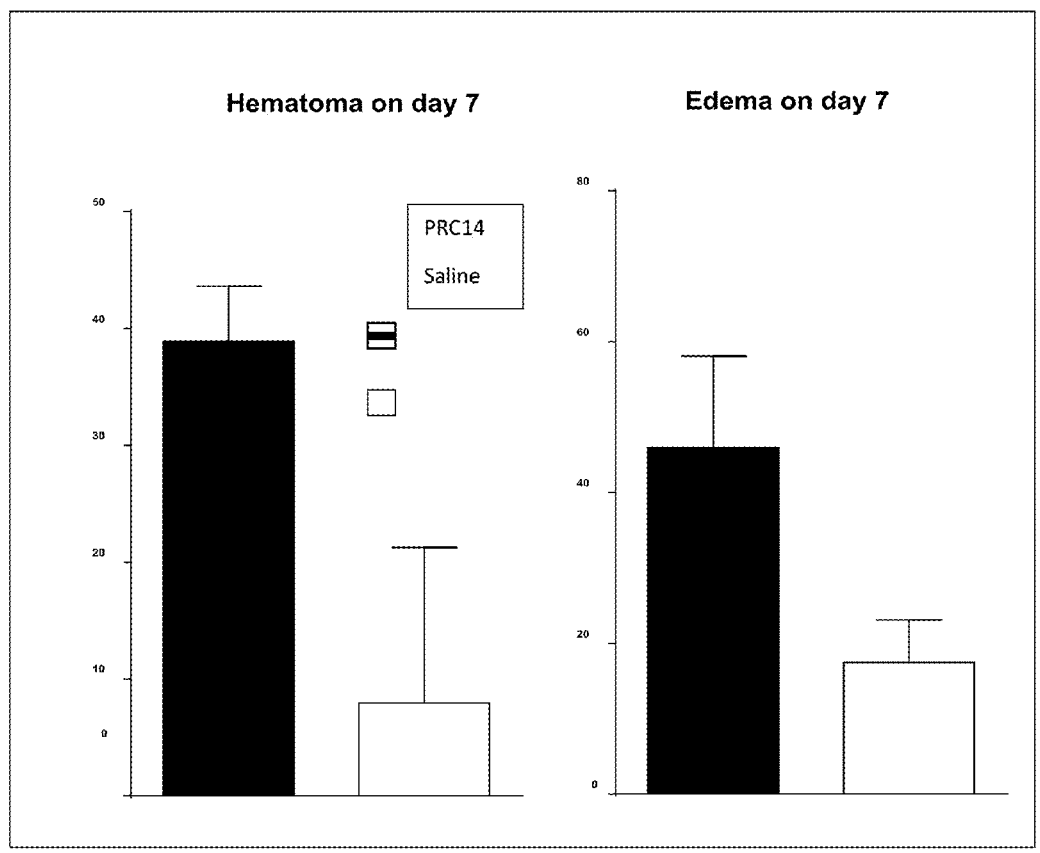
FIG. 22 Shows The results obtained using MRI on day 1 and 7, presented as percent of hematoma volume (left) or percent of edema volume (right) reduction between day 1 and day 7 after ICH in response to treatment with PRC14 (black filled bars) or saline (white filled bars).

Results. Using MRI on day 1 and 7, the hematoma volume and edema were determined. There were 7 control pigs and 6 pigs treated with PRC14. One pig assigned to PRC14 group died after the ICH surgical procedure, prior to initiation of treatment with PRC14. The results are presented as percent of hematoma volume (FIG. 22, left) or percent of edema volume (FIG. 22, right) reduction between day 1 and day 7 after ICH in response to treatment with PRC14 (black filled bars) or saline (white filled bars). By comparing hematoma volumes and edema volumes evolution between day 1 and day 7 post ICH, it was established that PRC14 effectively reduced both the hematoma (36.4% vs. 7.8%; p<0.05) and edema (45.9% vs. 7.5%; p<0.05) volume, as assessed using t-test. In addition, the hematoma volumes in all six PRC14-treated pigs was smaller at day 7 after ICH, as compared to hematoma volume at day 1 after ICH. However, among saline treated animals, 3 out of 7 pigs (42%) showed hematoma expansion. Hematoma volume was larger at day 7 as compared to day 1. This indicates that PRC14 treatment initiated at 6 after ICH (a highly reasonable therapeutic window of opportunity) in piglets, demonstrates ability to improve hematoma resolution and to reduce brain edema after ICH.

DEFINITIONS

It is to be understood that both the foregoing general description and the following detailed description are exemplary and explanatory only, and are not restrictive of the invention, as claimed. In this application, the use of the singular includes the plural, the word "a" or "an" means "at least one," and the use of "or" means "and/or," unless specifically stated otherwise. Furthermore, the use of the term "including," as well as other forms, such as "includes" and "included," is not limiting. Also, terms such as "element" or "component" encompass both elements or components comprising one unit and elements or components that comprise more than one unit unless specifically stated otherwise.

As used herein, the term "about," when used in conjunction with a percentage or other numerical amount, means plus or minus 10% of that percentage or other numerical amount. For example, the term "about 80%," would encompass 80% plus or minus 8%.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

As used herein, and unless otherwise indicated, the term intracranial hemorrhage (ICH) or ICH related disorder, includes but is not limited to, bleeding in the brain (intracerebral hemorrhage) as a result of trauma, non-traumatic intracranial hemorrhage that results from rupture or disease (including but, not limited to, amyloid angiopathy and vascular malformation) of blood vessels in the brain. Also included are primary and secondary (anticoagulant-induced) intra-cerebral hemorrhage, such as but not limited to hemorrhagic stroke which can result from inadequate blood-pressure control or and in some cases due to the use of anticoagulant, thrombolytic, and antiplatelet agents or any medications causing hypertension-induced bleeding, as well as other disorders that result in symptoms of brain edema or a neurological deficit.

As used herein, and unless otherwise indicated, the terms "treat," "treating," and "treatment" disclose an action that occurs while a patient is suffering ICH or ICH related disorders Where the context allows, the terms "treat," "treating," and "treatment" also refers to actions taken toward ensuring that individuals at increased risk of ICH, ICH related disorders or are suffering symptoms associated with ICH (such as but not limited to intracerebral hemorrhage, brain edema or a neurologic deficit) are able to receive appropriate surgical and/or other medical intervention prior to onset of ICH or ICH related disorders. As used herein, and unless otherwise indicated, the terms "prevent," "preventing," and "prevention" disclose an action that occurs before a patient begins to suffer from ICH or ICH related disorders that delays the onset of, and/or inhibits or reduces the severity of, ICH or ICH related disorders and symptoms (such as but not limited to brain edema or a neurologic deficit).

As used herein, and unless otherwise indicated, the terms "manage," "managing," and "management" encompass preventing, delaying, or reducing the severity of a recurrence of ICH or ICH related disorders and symptoms (such as but not limited to brain edema or a neurologic deficit) in a patient who has already suffered from such a disease or condition. The terms encompass modulating the threshold, development, and/or duration of the ICH or ICH related disorders or changing how a patient responds to the ICH or ICH related disorders.

As used herein, and unless otherwise specified, a "therapeutically effective amount" of a compound is an amount sufficient to provide any therapeutic benefit in the treatment or management of ICH or ICH related disorder, or to delay or minimize one or more symptoms associated with ICH or ICH related disorders (such as but not limited to brain edema or a neurologic deficit). A therapeutically effective amount of a compound means an amount of the compound, alone or in combination with one or more other therapies and/or therapeutic agents that provide any therapeutic benefit in the treatment or management of ICH or ICH related disorder or symptoms. The term "therapeutically effective amount" can encompass an amount that alleviates ICH or ICH related disorders, improves or reduces ICH or ICH related disorders, improves overall therapy, or enhances the therapeutic efficacy of another therapeutic agent.

As used herein, and unless otherwise specified, an effective amount of a compound is an amount sufficient to limit/prevent or delay the onset of ICH or ICH related disorder, or one or more symptoms (such as but not limited to brain edema or a neurologic deficit) associated with an ICH or ICH related disorder or prevents or delays its recurrence. A prophylactically effective amount of a compound means an amount of the compound, alone or in combination with one or more other treatment and/or prophylactic agent that provides a prophylactic benefit in the prevention of ICH or ICH related disorder. The term "prophylactically effective amount" encompasses an amount that limits/prevents ICH or ICH related disorder, improves overall prophylaxis, or enhances the prophylactic efficacy of another prophylactic agent. The prophylactically effective amount may be prescribed prior to, for example, the development of ICH or ICH related disorder.

As used herein, "patient" or "subject" includes mammalian organisms which are capable of suffering from ICH or ICH related disorder as described herein, such as human and non-human mammals, for example, but not limited to, rodents, mice, rats, non-human primates, companion animals, such as dogs and cats, as well as livestock, e.g., sheep, cow, horse, etc.

As used herein, "lactoferrin (LTF)" describes a polypeptide whose amino acid sequence has been derived from the naturally occurring lactoferrin, thus as used herein lactoferrin also encompasses recombinantly expressed native and non-native proteins and functional variants such as, but not limited to, those that are described in the following patents, patent applications and patent office publications: U.S. Pat. Nos. 6,066,469; 6,277,817; 6,440,690; 6,455,687; 6,569,831; 6,613,741; 7,691,809; 7,354,902; 8,334,254; US20030229925; US20030203839; US20110092411; WO1991013982; WO1995030339; WO1998050543; US20150093382, EP0603187; EP0644899; EP0871724 and EP1028977.

As used herein, "lactoferrin fusion protein" is a lactoferrin that has been significantly modified to improve activities, such as, but are not limited to increased solubility, bioavailability, prolong half-life in vivo, and/or to provide additional function, such as by fusion to a peptide (nucleic acid) that provides a label or enzymatic function. Examples include, but are not limited to, known lactoferrin fusion proteins, such as the recombinant fusion protein combining human LTF with the Fc fragment of IgG for neonatal Fc receptor (FcRn) such as that described in US patent publication US20150093382, as well as the recombinant human LTF-hIgG2-Fc fusion protein (identified as PRC14) described herein.

As used herein, the term "conservative substitution" generally refers to amino acid replacements that preserve the structure and functional properties of a protein or polypeptide. Such functionally equivalent (conservative substitution) peptide amino acid sequences include, but are not limited to, additions or substitutions of amino acid residues within the amino acid sequences encoded by a nucleotide sequence that result in a silent change, thus producing a functionally equivalent gene product. Conservative amino acid substitutions may be made on the basis of similarity in polarity, charge, solubility, hydrophobicity, hydrophilicity, and/or the amphipathic nature of the residues involved. For example: nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Without further elaboration, it is believed that one skilled in the art can, using the description herein, utilize the present invention to its fullest extent. The embodiments described herein are to be construed as illustrative and not as constraining the remainder of the disclosure in any way whatsoever. While the preferred embodiments have been shown and described, many variations and modifications thereof may be made by one skilled in the art without departing from the spirit and teachings of the invention. Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the embodiments of the present disclosure. The discussion of a reference is not an admission that it is prior art to the present disclosure, especially any reference that may have a publication date after the priority date of this application. The disclosures of all patents, patent applications, and publications cited herein are hereby incorporated by reference, to the extent that they provide exemplary, procedural, or other details supplementary to those set forth herein.

What is claimed is:

1. A recombinant polypeptide comprising:
   a lactoferrin sequence;
   an immunoglobulin IgG2 Fc domain sequence fused to said lactoferrin sequence; and
   an IgG2 hinge sequence, wherein said hinge is located between said lactoferrin sequence and said Fc domain sequence,
   wherein the amino acid sequence of said recombinant polypeptide has a sequence of SEQ ID NO: 2.

2. The polypeptide of claim 1, wherein the polypeptide is glycosylated to form a glycosylated polypeptide.

3. The polypeptide of claim 2, wherein the glycosylated polypeptide is N-linked.

4. A composition comprising the polypeptide of claim 1 in a pharmaceutically acceptable carrier, wherein said carrier is aqueous, powder, or saline, and wherein said composition is frozen or lyophilized.

5. A method of treating or preventing intracranial hemorrhage or a related disorder in a subject, comprising administering to said subject an effective amount of a composition comprising the polypeptide of claim 1, and wherein said polypeptide is administered intrathecally, buccally, orally, topically, intradermally, subcutaneously, intranasally, intramuscularly, intravenously, intra-arterially, or directly into a tissue site.

6. The method of claim 5, wherein said related disorder is a cognitive or neurological deficit, inflammation, infection, edema or brain atrophy due to intracranial hemorrhage.

7. An isolated recombinant polynucleotide molecule comprising a coding sequence for a polypeptide comprising:
   a lactoferrin coding sequence;
   an immunoglobulin IgG2 Fc domain coding sequence fused to said lactoferrin coding sequence; and an IgG2 hinge coding sequence, wherein said hinge is located between said lactoferrin coding sequence and said Fc domain coding sequence; and wherein polypeptide has a sequence of SEQ ID NO: 2.

8. The polynucleotide of claim 7, wherein the nucleic acid sequence of said polynucleotide comprises SEQ ID NO: 1.

9. An expression vector comprising a heterologous promoter sequence linked to a polynucleotide of claim 7.

10. The expression vector of claim 9, wherein said vector is expressed in a mammalian cell, a CHO cell, a yeast cell, or an insect cell.

11. A host cell, comprising a polynucleotide molecule of claim 7.

* * * * *